US006525127B1

(12) United States Patent
Jariwala et al.

(10) Patent No.: US 6,525,127 B1
(45) Date of Patent: *Feb. 25, 2003

(54) ALKYLATED FLUOROCHEMICAL OLIGOMERS AND USE THEREOF IN THE TREATMENT OF FIBROUS SUBSTRATES

(75) Inventors: Chetan P. Jariwala, Woodbury, MN (US); James D. Eggleston, St. Paul, MN (US); Michael A. Yandrasits, Hastings, MN (US); Rudolf J. Dams, Antwerp (BE)

(73) Assignee: 3M Innovative Properties Company, St. Paul, MN (US)

( * ) Notice: Subject to any disclaimer, the term of this patent is extended or adjusted under 35 U.S.C. 154(b) by 72 days.

This patent is subject to a terminal disclaimer.

(21) Appl. No.: 09/708,372

(22) Filed: Nov. 8, 2000

Related U.S. Application Data

(63) Continuation-in-part of application No. 09/309,836, filed on May 11, 1999, now Pat. No. 6,288,157.

(51) Int. Cl.$^7$ .............................................. C08K 5/02
(52) U.S. Cl. ........................ 524/462; 524/544; 524/560; 525/199; 525/200; 525/276
(58) Field of Search ................ 524/462, 544, 524/560; 525/276, 199, 200

(56) References Cited

U.S. PATENT DOCUMENTS

| | | | |
|---|---|---|---|
| 2,803,615 A | 8/1957 | Ahlbrecht et al. | 260/29.6 |
| 2,803,656 A | 8/1957 | Ahlbrecht et al. | 260/556 |
| 2,841,573 A | 7/1958 | Ahlbrecht et al. | 260/79.3 |
| 3,758,447 A | 9/1973 | Falk et al. | 260/78.5 |
| 3,890,271 A | 6/1975 | Kokoszka | 260/46.5 |
| 3,899,563 A | 8/1975 | Oxenrider et al. | 264/211 |
| 3,923,715 A | 12/1975 | Dettre et al. | 260/29.6 |
| 3,960,575 A | 6/1976 | Martin | 106/10 |
| 3,971,373 A | 7/1976 | Braun | 128/146.2 |
| 4,100,324 A | 7/1978 | Anderson et al. | 428/288 |
| RE30,782 E | 10/1981 | van Turnhout | 264/22 |
| 4,302,366 A | 11/1981 | Perronin et al. | 252/8.6 |
| 4,375,718 A | 3/1983 | Wadsworth et al. | 29/592 |
| RE31,285 E | 6/1983 | van Turnhout et al. | 55/155 |
| 4,429,001 A | 1/1984 | Kolpin et al. | 428/283 |
| 4,525,305 A | 6/1985 | Patel | 260/401 |
| 4,539,006 A | 9/1985 | Langford | 8/94.1 |
| 4,588,537 A | 5/1986 | Klaase et al. | 264/22 |
| 4,592,815 A | 6/1986 | Nakao | 204/165 |
| 4,619,976 A | 10/1986 | Morriss et al. | 525/439 |
| 4,709,074 A | 11/1987 | Bathelt et al. | 560/33 |
| 4,778,915 A | 10/1988 | Lina et al. | 560/29 |
| 4,782,175 A | 11/1988 | Wehowsky et al. | 560/26 |
| 4,843,134 A | 6/1989 | Kotnour et al. | 526/318.4 |
| 4,873,306 A | 10/1989 | Wehowsky et al. | 528/28 |
| 4,920,190 A | 4/1990 | Lina et al. | 526/288 |
| 4,931,062 A | 6/1990 | Bay et al. | 8/94.23 |
| 5,025,052 A | 6/1991 | Crater et al. | 524/104 |
| 5,098,446 A | 3/1992 | Rodriguez et al. | 8/94.26 |

(List continued on next page.)

FOREIGN PATENT DOCUMENTS

| | | |
|---|---|---|
| EP | 324345 | 4/1992 |
| EP | 298364 | 10/1993 |
| EP | 372746 | 8/1994 |
| EP | 613462 | 1/1996 |
| EP | 682044 | 6/1999 |
| JP | 3041160 | 2/1991 |
| JP | 9323956 | 12/1997 |
| WO | WO 92/15732 | 9/1992 |
| WO | WO 94/01587 | 1/1994 |
| WO | WO 94/12561 | 6/1994 |
| WO | WO 97/07272 | 2/1997 |
| WO | WO 97/22576 | 6/1997 |
| WO | WO 97/22659 | 6/1997 |
| WO | WO 97/22660 | 6/1997 |
| WO | WO 98/15598 | 4/1998 |
| WO | WO 98/20170 | 5/1998 |
| WO | WO 98/51723 | 11/1998 |
| WO | WO 98/51724 | 11/1998 |
| WO | WO 98/51725 | 11/1998 |
| WO | WO 98/51726 | 11/1998 |
| WO | WO 98/51727 | 11/1998 |
| WO | WO 99/05345 | 2/1999 |
| WO | WO 99/14380 | 3/1999 |

OTHER PUBLICATIONS

Kirk–Othmer, Encyclopedia of Chemical Technology, 4th Ed., vol. 25, (1998) pp. 595–614.

H.C. Fielding, "Organofluorine Chemicals and Their Industrial Applications", R.E. Banks, Ed., Society of Chemical Industry, 1979, pp. 214–234.

Chujo et al., J. Polymer Science, Part A, 1988, 26, 2991.

Van Wente et al., "Manufacture of Super Fine Organic Fibers", Report No. 4364 of the Naval Research Laboratories, May 25, 1954.

C.N. Davies, "The Separation of Airborne Dust and Particles", Institution of Mechanical Engineers, London, Proceedings IB, 1952.

Van Wente, "Superfine Thermoplastic Fibers", Industrial Engineering Chemistry, vol. 48, 1956, pp. 1342–1346.

Primary Examiner—Edward J. Cain
(74) Attorney, Agent, or Firm—Kent S. Kokko

(57) ABSTRACT

This invention provides a method of treating fibrous substrates, such as leather, by contacting the substrate with a fluorochemical compound comprising: a fluorochemical oligomeric portion comprising an aliphatic backbone with a plurality of pendant fluoroaliphatic groups, each fluoroaliphatic group having a fully fluorinated terminal group and each independently linked to a carbon atom of the aliphatic backbone through an organic linking group; an aliphatic moiety; and a linking group which links the fluorochemical oligomeric portion to the aliphatic moiety. The fluorochemical compounds provide desirable oil, water and stain repellency to fibrous substrates.

27 Claims, No Drawings

U.S. PATENT DOCUMENTS

| | | | |
|---|---|---|---|
| 5,124,181 A | 6/1992 | Schaffer et al. | 427/323 |
| 5,143,963 A | 9/1992 | Sterling et al. | 524/366 |
| 5,145,727 A | 9/1992 | Potts et al. | 428/198 |
| 5,149,576 A | 9/1992 | Potts et al. | 428/198 |
| 5,292,796 A | 3/1994 | Dams et al. | 524/598 |
| 5,300,357 A | 4/1994 | Gardiner | 428/224 |
| 5,300,587 A | 4/1994 | Mascia et al. | 525/359.3 |
| 5,314,959 A | 5/1994 | Rolando et al. | 525/276 |
| 5,336,717 A | 8/1994 | Rolando et al. | 525/64 |
| 5,380,778 A | 1/1995 | Buckanin | 524/247 |
| 5,411,576 A | 5/1995 | Jones et al. | 95/57 |
| 5,420,015 A | 5/1995 | Wuerch | 106/162 |
| 5,451,622 A | 9/1995 | Boardman et al. | 524/100 |
| 5,453,540 A | 9/1995 | Dams et al. | 564/96 |
| 5,459,188 A | 10/1995 | Sargent et al. | 524/319 |
| 5,496,507 A | 3/1996 | Angadjivand et al. | 264/423 |
| 5,508,330 A | 4/1996 | Coughlin et al. | 524/251 |
| 5,534,604 A | 7/1996 | Bildhauer | 526/253 |
| 5,536,157 A | 7/1996 | Linz | 425/72.2 |
| 5,567,343 A | 10/1996 | Ritter et al. | 252/857 |
| 5,681,963 A | 10/1997 | Liss | 548/455 |
| 5,705,592 A | 1/1998 | Sejpka et al. | 528/42 |
| 5,741,434 A | 4/1998 | Ritter et al. | 252/8.57 |
| 6,174,964 B1 | 1/2001 | Jariwala et al. | 525/276 |

ALKYLATED FLUOROCHEMICAL OLIGOMERS AND USE THEREOF IN THE TREATMENT OF FIBROUS SUBSTRATES

CROSS-REFERENCE TO RELATED APPLICATION

This is a continuation-in-part of application No. 09/309,836, filed May 11, 1999 now U.S. Pat. No. 6,288,157.

This invention relates to fluorochemical compositions for use in providing repellent properties to a fibrous substrate material. In another aspect, this invention relates to fluorochemical compounds that contain pendent fluoroaliphatic groups proximal to one another. In yet another aspect, it relates to fluorochemical compounds that are at least in part oligomeric in nature.

The utility of organofluorine compounds as surface-active agents (i.e., surfactants) and surface-treating agents is due in large part to the extremely low free-surface energy of a $C_6$–$C_{12}$ fluorocarbon group, according to H. C. Fielding, "Organofluorine Compounds and Their Applications," R. E. Banks, Ed., Society of Chemical Industry at p. 214 (1979). Generally, the organofluorine substances described above are those which have carbon-bonded fluorine in the form of a monovalent fluoroaliphatic radical such as a perfluoroalkyl group, typically —$C_nF_{2n+1}$, where n is at least 3, the terminal part of which group is trifluoromethyl, —$CF_3$.

U.S. Pat. No. 3,758,447 (Falk et al.) describes polymers that result from free radical polymerization of a monomer in the presence of perfluoroalkyl mercaptans, which act as chain-transfer agents. Mercaptans that contain pairs or triplets of closely-packed perfluoroalkyl groups are said to produce polymers with higher oil repellency levels compared with analogous polymers derived from a mercaptan with just one perfluoroalkyl group or perfluoroalkyl groups that are not closely packed.

U.S. Pat. No. 5,453,540 (Dams et al.) describes fluorochemical compositions for the treatment of textiles comprising: (i) a fluorochemical oligomeric portion comprising an aliphatic backbone with a plurality of fluoroaliphatic groups attached thereto, each fluoroaliphatic group having a fully fluorinated terminal group and each independently linked to a carbon atom of the aliphatic backbone through an organic linking group;(ii) an organic moiety (which can be functional or non-functional, and which is different from the fluorochemical oligomeric portion); (iii) a non-polymeric isocyanate-derived linking group which links the fluorochemical oligomeric portion to the organic moiety; and (iv) a group bonded thereto, which can impart soft hand, stain release, water repellency, or a durable property when the compound is applied to a fibrous substrate.

J. Polymer Science, Part A 1988, 26, 2991 (Chujo et al.) describes a di-carboxyl terminated macromonomer prepared by the free radical co-polymerization of a perfluoroalkylethyl acrylate and methyl methacrylate in the presence of thiomalic acid. Also described is the reaction of such macromonomers with organic dicarboxylic acids and organic diamines in the presence of an appropriate catalyst to afford a copolymer wherein the macromonomer is grafted onto a polyamide chain.

The treatment of hides and skins to form leather involves a number of interdependent chemical and mechanical operations. These operations may be divided into a sequence of "wet end" steps followed by a sequence of "dry" steps. A description of each of these operations is provided in Fundamentals of Leather Manufacturing, Prof Dr Heidemann (Eduard Roether KG, 1993). The primary tanning operation involves the treatment of the hide to preserve it and form useful leather. Chrome tanning salts are well known and widely used for this purpose. Chrome-tanned hides or skins are known in the art as "wet blue leather". In order to produce a uniform piece of leather with the required physical and aesthetic properties, a second tanning step, known as "retanning" is employed. Retanning can be accomplished using a variety of naturally derived materials including extracts from vegetables or plants, and synthetic tanning agents known as "syntans", or combinations thereof. After or during retanning, the leather can be colored and fatliquored.

A number of publications have proposed various copolymers for treating leather during tanning and retanning, addressing the problem of making treated leather more water resistant or completely waterproof.

EP-A-372 746 discloses a method and process for treating leather utilizing selected amphiphilic copolymers for improving the strength, temper and water resistance of the leather. The amphiphilic copolymers are formed from a predominant amount of at least one hydrophobic monomer and a minor amount of at least one copolymerizable hydrophilic monomer. The application states that the process may be particularly useful as a one step substitute for conventional retanning and fatliquoring treatment steps.

EP-A-682 044 discloses copolymers comprising ethylenically unsaturated dicarboxylic acid anhydrides, long chain olefins and fluorolefins. Leathers treated with these polymers are shown to yield good waterproofness results according to the Bally-Penotrometer test.

U.S. Pat. No. 5,124,181 discloses copolymers which contain a) from 50 to 90% by weight of $C_8$–$C_{40}$-alkyl methacrylates, vinyl esters of $C_8$–$C_{40}$-carboxylic acids or mixtures thereof and b) from 10 to 50% by weight of monoethylenically unsaturated $C_3$–$C_{12}$-carboxylic acids, monoethylenically unsaturated dicarboxylic anhydrides, monoesters or monoamides of monoethylenically unsaturated $C_4$–$C_{12}$-dicarboxylic acids, amides of $C_3$–$C_{12}$-monocarboxylic acids or mixtures thereof as copolymerized units and which have molecular weights of from 500 to 30,000. The copolymers are used in at least partially neutralized form in aqueous solution or dispersion for making leather and furs water repellent.

WO 94/01587 discloses water-dispersible and/or water-emulsifiable co-oligomers containing (a) fatty crotonates; (b) radically copolymerizable, hydrophilic, ethylenically unsaturated acids and/or their anhydrides, and possibly (c) minor amounts of other copolymerizable comonomers. These co-oligomers are used as amphiphilic agents for greasing leather and pelts.

Despite the various publications there continues to be a need for further fluorochemical compositions for the treatment of leather to impart desired properties thereto such as water repellency, water proofness, oil repellency and stain resistance. It is further desired that such fluorochemical compositions be readily produced in a cost effective way, have sufficient storage stability and are efficient even if applied in low quantities to the substrate. Highly desired fluorochemical compositions are those that can impart both good water repellency as well as oil repellency to leather substrates. In one aspect, the present invention relates to the wet end operations which take place after primary tanning, namely retanning and fatliquoring.

SUMMARY OF THE INVENTION

This invention provides a method of treating fibrous substrates comprising contacting the fibrous substrate with a composition comprising alkylated fluorochemical oligomeric compounds comprising:
(i) a fluorochemical oligomeric portion comprising an aliphatic backbone with a plurality of pendant fluoroaliphatic groups, each fluoroaliphatic group having a fully fluorinated terminal group and each independently linked to a carbon atom of the aliphatic backbone through an organic linking group;
(ii) an aliphatic moiety having at least 12 carbon atoms; and
(iii) a linking group which links the fluorochemical oligomeric portion to the aliphatic moiety.

In another aspect, the invention provides a method of treating fibrous substrates comprising contacting the fibrous substrate with a composition comprising alkylated fluorochemical oligomeric compounds comprising:
(i) an oligomeric portion having both fluoroaliphatic and fluorine-free aliphatic pendent groups;
(ii) an aliphatic moiety having at least 12 carbon atoms; and
(iii) a linking group which links the oligomeric portion to the aliphatic moiety;

In another aspect, the present invention provides a fluorochemical leather treatment composition comprising at least one fluorochemical compound described herein. In another aspect, the present invention provides a treated substrate comprising a coating of the treatment composition on at least a portion of the substrate.

Preferably, the fluorochemical oligomeric compounds exhibit a receding contact angle, to hexadecane, of at least 30°, as defined by the test method described herein. Such compounds have improved anti-staining properties, as well as desirable oil- and water-repellent properties.

The composition comprising alkylated fluorochemical oligomeric compounds can be applied in the form of an aqueous dispersion or emulsion, or as a solution thereof in an organic solvent. The aqueous dispersions are preferred for environmental reasons. Application of the composition onto a substrate may be done by spraying, padding, roll coating, brushing or exhausting the composition onto a substrate and drying the treated substrate.

DETAILED DESCRIPTION

The alkylated fluorochemical oligomers in a composition useful in the invention generally contain a plurality of pendant fluoroaliphatic groups proximal to one another (e.g., located on alternating carbon atoms of an aliphatic backbone, or occasionally on adjacent carbon atoms), as distinct from isolated fluoroaliphatic groups randomly distributed throughout the compound and also as distinct from fluoroaliphatic groups uniformly located on adjacent carbon atoms.

In other preferred embodiments, the invention provides a method of treating fibrous substrates comprising contacting the substrate with fluorochemical compositions comprising fluorinated compounds of Formulas I or II

   I

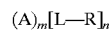   II wherein
m is 1 to 4 inclusive;
n is 1 to 4 inclusive;
each L independently comprises a linking group;
R is a saturated or unsaturated aliphatic moiety of 12 to 75 carbon atoms; and A is a fluorochemical oligomeric portion of the formula:

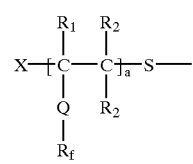   III wherein
a is a number such that A is oligomeric and comprises a plurality of pendent $R_f$ groups;
each $R_1$ is independently hydrogen, halogen, or straight chain or branched chain alkyl containing 1 to about 4 carbon atoms;
each $R_2$ is independently hydrogen or straight chain or branched chain alkyl containing 1 to about 4 carbon atoms;
each Q is a covalent bond or an organic linking group, such as a sulfonamidoalkylene group;
$R_f$ is a fluoroaliphatic group, such as $-(CF_2)_7CF_3$, that comprises a fully fluorinated terminal group;
X is a hydrogen atom or a group derived from a free radical initiator (e.g. t-butoxy).

A may further comprise a fluorochemical oligomeric portion of Formula IV:

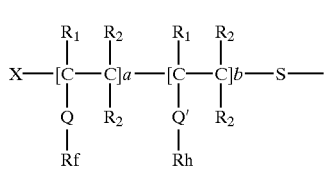   IV wherein the sum of a+b is a number such that A is oligomeric,
each $R_1$ is independently hydrogen, halogen, or straight chain or branched chain alkyl containing 1 to about 4 carbon atoms;
each $R_2$ is independently hydrogen or straight chain or branched chain alkyl containing 1 to about 4 carbon atoms;
Q and Q' are each independently a covalent bond or an organic linking group,
$R_f$ is a fluoroaliphatic group, such as $-(CF_2)_3CF_3$, that comprises a fully fluorinated terminal group;
$R_h$ is a fluorine-free aliphatic group; preferably having 6 or fewer carbon atoms.

Preferably, with reference to Formulas I and II, both m and n are one to produce an alkylated oligomeric fluorochemical of the Formulas V or VI:

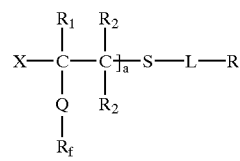   V

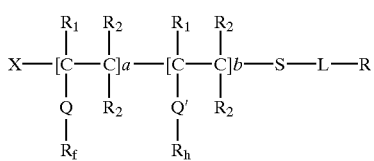

VI

Preferably the ratio of a:b is 4:1 or more.

With reference to Formulas III to VI, it will be understood that the oligomer may have a random distribution of fluorinated and fluorine-free segments, or preferably a sequential arrangement where the oligomer comprises "blocks" of fluorinated and fluorine-free segments, i.e. a block copolymer. Further it will be understood that the relative position of the units derived from fluorinated monomers and fluorine-free monomers may vary with respect to the X and S moieties. In essence the following structures are both within the scope of the invention:

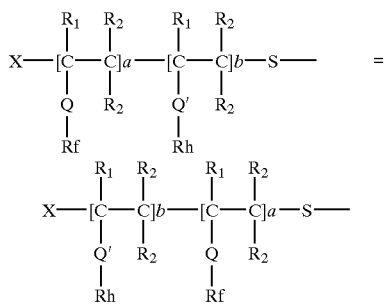

As described above and further illustrated in Formulas I–VI, a fluorochemical composition useful in the invention comprises an alkylated fluorochemical oligomeric compound that generally has three principal portions: a fluorochemical oligomeric portion "A", a linking group "L", and an aliphatic moiety "R". The fluorochemical oligomeric portion and the organic moiety are linked together by linking group L. The linking group may be a covalent bond, may result from a condensation reaction between a nucleophile, such as an alcohol, an amine, or a thiol, and an electrophile such as a carboxylic acid, ester, acyl halide, sulfonate ester, sulfonyl halide, cyanate, isocyanate, or may result from a nucleophilic displacement reaction between a nucleophile, such as previously described, and a moiety bearing a leaving group, such as the reaction between an alcohol (or alkoxide) and an alkyl halide (where the halogen atom of the alkyl halide serves as a leaving group).

Examples of suitable linking groups L include a covalent bond, straight chain, branched chain, or cyclic alkylene, arylene, aralkylene, oxy, oxo, hydroxy, thio, sulfonyl, sulfoxy, amino, imino, sulfonamido, carboxamido, carbonyloxy, urethanylene, ureylene, and combinations thereof such as sulfonamidoalkylene.

A salient component of the fluorochemical oligomeric portion is the fluoroaliphatic group, designated herein as $R_f$. The fluorinated compound of the invention contains a plurality of pendent $R_f$ groups (e.g., from 2 to about 10) proximal to one another and preferably contains from about 5 percent to about 80 percent, more preferably from about 20 percent to about 65 percent, and most preferably about 25 percent to about 55 percent fluorine by weight, based on the total weight of the compound, the loci of the fluorine being essentially in the $R_f$ groups. $R_f$ is a stable, inert, non-polar, preferably saturated, monovalent moiety which is both oleophobic and hydrophobic. $R_f$ preferably contains at least about 3 carbon atoms, more preferably 3 to about 20 carbon atoms, and most preferably about 4 to about 8 carbon atoms. $R_f$ can contain straight chain, branched chain, or cyclic fluorinated alkylene groups or combinations thereof or combinations thereof with straight chain, branched chain, or cyclic alkylene groups. $R_f$ is preferably free of polymerizable olefinic unsaturation and can optionally contain catenary heteroatoms such as divalent oxygen, or trivalent nitrogen. It is preferred that $R_f$ contain about 35% to about 78% fluorine by weight, more preferably about 40% to about 78% fluorine by weight. The terminal portion of the $R_f$ group contains a fully fluorinated terminal group. This terminal group preferably contains at least 7 fluorine atoms, e.g., $CF_3CF_2CF_2$—, $(CF_3)_2CF$—, or the like. Perfluorinated aliphatic groups (i.e., those of the formula $C_oF_{2o+1}$, where o is 4 to 8 are the most preferred embodiments of $R_f$.

The aliphatic backbone of the fluorochemical oligomeric portion comprises a sufficient number of polymerized units to render the portion oligomeric. The aliphatic backbone preferably comprises from 2 to about 10 polymerized units ("a" and "b" in Formula III to VI) derived from fluorinated monomers (i.e., monomers containing a fluorinated organic group $R_f$ as defined above), it is more preferred that the aliphatic backbone comprise from 3 to about 8, most preferably about 4, polymerized units.

The fluorochemical compositions of the invention generally comprise mixtures of alkylated fluorochemical oligomeric compounds. Accordingly, compounds are sometimes referred to herein as having non-integral numbers of particular substituents (e.g., "a=2.7"). In such cases the number indicates an average and is not intended to denote fractional incorporation of a substituent. The terms "oligomer" or "oligomeric" when used herein designate compounds containing a plurality of polymerized units, but fewer than that number of polymerized units present in a polymer (e.g., chains of 2 to about 10 polymerized units are to be considered "oligomeric").

The fluoroaliphatic group $R_f$ and the fluorine-free aliphatic group are each linked to the organic portion (i.e. the oligomeric backbone or the unsaturated portion of the monomer) by a linking groups designated as Q and Q' respectively in the Formulas III to VI used herein. Q and Q' are independently linking groups that may be a covalent bond, divalent alkylene, or a group that can result from the condensation reaction of a nucleophile such as an alcohol, an amine, or a thiol with and electrophile, such as an ester, acid halide, isocyanate, sulfonyl halide, sulfonyl ester, or may result from a displacement reaction between a nucleophile and leaving group. Each Q and Q' is are independently chosen, preferably contains from 1 to about 20 carbon atoms and can optionally contain catenary oxygen, nitrogen, sulfur, or silicon-containing groups or a combination thereof Q and Q' is preferably free of functional groups that substantially interfere with free-radical oligomerization (e.g., polymerizable olefinic double bonds, thiols, easily abstracted hydrogen atoms such as cumyl hydrogens, and other such functionality known to those skilled in the art). Examples of suitable linking groups Q and Q' include straight chain, branched chain, or cyclic alkylene, arylene, aralkylene; oxy, oxo, hydroxy, thio, sulfonyl, sulfoxy, amino, imino, sulfonamido, carboxamido, carbonyloxy, urethanylene, urylene, and combinations thereof such as sulfonamidoalkylene. Preferably linking group Q is a covalent bond or a sulfonamidoalkylene group. Preferably linking group Q' is a covalent bond.

Suitable linking groups Q and Q' include the following structures in addition to a covalent bond. For the purposes of this list, each k is independently an integer from 0 to about 20, $R_1'$ is hydrogen, phenyl, or alkyl of 1 to about 4 carbon atoms, and $R_2'$ is alkyl of 1 to about 20 carbon atoms. Each structure is non-directional, i.e. —$(CH_2)_kC(O)O$— is equivalent to —$O(O)C(CH_2)_k$—.

| | |
|---|---|
| —$SO_2NR_1'(CH_2)_kO(O)C$— | —$CONR_1'(CH_2)_kO(O)C$— |
| —$(CH_2)_kO(O)C$— | —$CH_2CH(OR_2')CH_2O(O)C$— |
| —$(CH_2)_kC(O)O$— | —$(CH_2)_kSC(O)$— |
| —$(CH_2)_kO(CH_2)_kO(O)C$— | —$(CH_2)_kS(CH_2)_kO(O)C$— |
| —$(CH_2)_kSO_2(CH_2)_kO(O)C$— | —$(CH_2)_kS(CH_2)_kOC(O)$— |
| —$(CH_2)_kSO_2NR_1'(CH_2)_kO(O)C$— | —$(CH_2)_kSO_2$— |
| —$SO_2NR_1'(CH_2)_kO$— | —$SO_2NR_1'(CH_2)_k$— |
| —$(CH_2)_kO(CH_2)_kC(O)O$— | —$(CH_2)_kSO_2NR_1'(CH_2)_kC(O)O$— |
| —$(CH_2)_kSO_2(CH_2)_kC(O)O$— | —$CONR_1'(CH_2)_kC(O)O$— |
| —$(CH_2)_kS(CH_2)_kC(O)O$— | —$CH_2CH(OR_2')CH_2C(O)O$— |
| —$SO_2NR_1'(CH_2)_kC(O)O$— | —$(CH_2)_kO$— |
| —$(CH_2)_kNR_1'C(O)O$— | —$OC(O)NR'(CH_2)_k$— |
| —$(CH_2)_kO(O)C$— | —$CH_2CH(OR_2')CH_2C(O)O$— |
| —$(CH_2)_kC(O)O$— | —$(CH_2)_kO$— |
| —$(CH_2)_kO(CH_2)_kO(O)C$— and | a covalent bond |

The organic aliphatic moiety, designated R in compounds of Formulas I–VI is a mono-, di-, tri- or tetravalent, linear or branched chain, saturated or unsaturated, cyclic or acyclic (or any combination thereof) organic aliphatic group having from 12 to 75 carbon atoms. In certain embodiments R may be fluorinated (i.e. R =$R_f$). The valency is equivalent to the value of n in Formula I and is equal to 1 in Formula II. The range of structures contemplated for the organic moiety R will be better understood with reference to the compounds suitable for use in steps of the Reaction Schemes described in detail below. Preferably R is a monovalent alkyl group having from 12 to 75 carbon atoms, preferably 16 to 60 carbon atoms. Where more than one R group is present, such as in Formula II, or when n is greater than one in Formula I, the sum of the carbon atoms in the R groups is preferably from 12 to 100 carbon atoms.

The fluorinated compounds and fluorochemical compositions useful in the invention will be illustrated with reference to the embodiments shown in Formulas I–VI. In such embodiments, linking group L links the fluorochemical oligomeric portion A to the aliphatic group R. Each linking group L may be a covalent bond, a di- or polyvalent alkylene group, or a group that can result from the condensation reaction of a nucleophile such as an alcohol, an amine, or a thiol with an electrophile, such as an ester, acid halide, isocyanate, sulfonyl halide, sulfonyl ester, or may result from a displacement reaction between a nucleophile and leaving group. Each L is independently chosen, preferably contains from 1 to about 20 carbon atoms and can optionally contain catenary (i.e. in-chain) oxygen, nitrogen, sulfur, or silicon-containing groups or a combination thereof, L is preferably free of functional groups that substantially interfere with free-radical oligomerization (e.g., polymerizable olefinic double bonds, thiols, easily abstracted hydrogen atoms such as cumyl hydrogens, and other such detrimental functionalities known to those skilled in the art). Examples of suitable linking groups L include straight chain, branched chain, or cyclic alkylene, arylene, aralkylene, oxy, oxo, sulfonyl, sulfoxy, amino, imino, sulfonamido, carboxamido, carbonyloxy, urethanylene, ureylene, and combinations thereof such as sulfonamidoalkylene. In addition to a covlaent bond, preferred L groups include the following structures (including combinations and multiples thereof) wherein each k is independently an integer from 0 to about 20, $R_2'$ is alkyl of 1 to about 20 carbon atoms.

Returning now to Formulas III to VI above, $R_1$ is hydrogen, halogen (e.g., fluoro, chloro, bromo), or straight chain or branched chain alkyl of 1 to about 4 carbon atoms (e.g., methyl, ethyl, propyl, isopropyl, butyl, isobutyl, and the like). Each $R_2$ is independently hydrogen or straight chain or branched chain alkyl of 1 to about 4 carbon atoms.

X is a group derived from a free-radical initiator. As used herein, the term "free-radical initiator" designates any of the conventional compounds such as organic azo compounds, organic peroxides (e.g., diacyl peroxides, peroxyesters, dialkyl peroxides) and the like that provide initiating radicals upon homolysis. As used herein, the term "group derived from a free-radical initiator" designates an initiating radical formed upon homolytic decomposition of a free-radical initiator.

Suitable groups X include non-reactive groups such as a hydrogen atom, t-butoxy (derived from di-t-butylperoxide), and benzoyloxy (derived from benzoyl peroxide), and reactive groups such as —$CCH_3(CN)CH_2CH_2CO_2H$ (derived from azo-4-cyanoisovaleric acid), —$C(CH_3)_2CN$ (derived from azoisobutyronitrile), and those derived from other known functional azo compounds such as 2,2'-azobis[N-(4-chlorophenyl)-2-methylpropionamidine]-dihydrochloride; 2,2'-azobis[N-(4-hydroxyphenyl)-2-methylpropionamidine] dihydrochloride; 2,2,-azobis[N-(4-aminophenyl)-2-methylpropionamidine]-tetrahydrochloride; 2,2'-azobis[2-methyl-N-2-propenylpropionamidine]dihydrochloride; 2,2'-azobis[N-(2-hydroxyethyl)-2-methylpropionamidine]-dihydrochloride; 2,2'-azobis[2-methyl-N-(2-hydroxyethyl)-propionamide]; 2,2'-azobis[2-(hydroxymethyl) propionitrile]; 2,2'-azobis[2-methyl-N-[1,1-bis(hydroxymethyl)-2-hydroxyethyl]propionamide]; and 2,2'-azobis{2-methyl-N-[1,1-bis(hydroxymethyl)ethyl]-propionamide}. Preferred groups X include those enumerated above.

Surprisingly, it has been found that a strong correlation exists between oil receding contact angle and anti- oil staining properties for fluorochemical oligomers when they are used as leather treatments. Consequently, receding contact angle measurements may be used to readily identify fluorochemical materials having particularly good anti-staining properties, without having to conduct lengthy staining tests on fluorochemical emulsion-treated leather substrates. Compositions having a low receding contact angle measurement generally show poor performance to oil staining. For the purposes of the present invention, fluorochemical oligomers having a receding contact angle to n-hexadecane of at least about 30°, preferably greater than about 40°, and more preferably at least about 50° are found to exhibit particularly good anti-oil staining properties.

The fluorochemical compounds of Formulas III and V can be prepared by oligomerization of an unsaturated, fluorinated compound (V) in the presence of a free-radical initiator and chain-transfer agent of the formula $L(SH)_m$ (m=1–4) according to the following Scheme:

Scheme 1

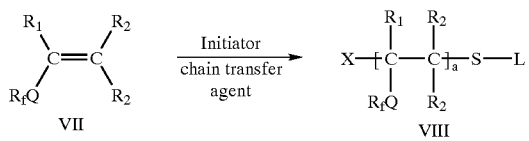

The fluorochemical compounds of Formulas IV and VI can be prepared by oligomerization of an unsaturated compound having a fluorinated aliphatic pendent group (VII) and an unsaturated compound having a fluorine-free aliphatic pendent group (IX) in the presence of a free-radical initiator and chain-transfer agent of the formula $L(SH)_m$ (for m=1) according to the following Scheme:

Scheme 2

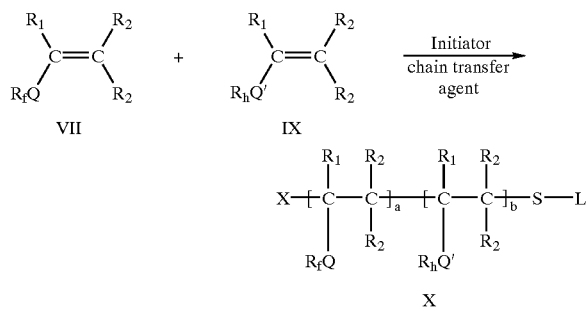

The moiety "L" corresponds to the linking group moiety L of Formula V or VI.

When the chain-transfer agent contains more than one sulfhydryl group, multiple fluoroaliphatic groups A may be linked through linking groups L to one or more aliphatic R groups. For examples, when the chain transfer agent contains two sulfhydryl groups, two fluoroaliphatic groups A may be linked to L as follows:

Scheme 3

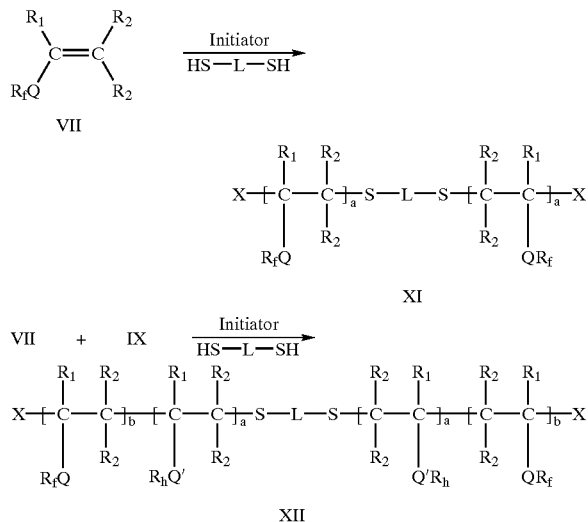

Compounds of Formula (VII) and methods for the preparation thereof are known and disclosed, e.g., in U.S. Pat. Nos. 2,803,615 (Ahlbrecht et al.) and 2,841,573 (Ahlbrecht et al.) which disclosures are incorporated herein by reference. Examples of such compounds include general classes of fluorochemical monomers such as acrylates, methacrylates, vinyl ethers, and allyl compounds containing fluorinated sulfonamido groups, acrylates or methacrylates derived from fluorochemical telomer alcohols, fluorochemical thiols, and the like. Preferred compounds of Formula VII include N-methyl perfluorobotanesulfonamidoethyl acrylate, N-methyl perfluorooctanesulfonamidoethyl methacrylate, N-ethyl perfluorooctanesulfonamidoethyl acrylate, N-ethyl perfluorohexylsulfonamidoethyl methacrylate, the reaction product of isocyanatoethyl methacrylate and N-methylperfluorooctanesulfonamidoethyl alcohol, 1,1-dihydroperfluorooctyl acrylate, N-methyl perfluorooctanesulfonamidoethyl vinyl ether, $C_4F_9SO_2NHCH_2CH=CH_2$, and others such as perfluorocyclohexyl acrylate (c-$C_6F_{11}CH_2OCOCH=CH_2$), and tetrameric hexafluoropropyleneoxide dihydroacrylate.

Compounds of Formula IX may be selected from alkyl acrylate esters, vinyl acetate, styrene, alkyl vinyl ethers, alkyl methacrylate esters, acrylic acid, methacrylic acid, acrylamide, methacrylamide, acrylonitrile, methacrylonitrile, and N-vinylpyrrolidone. Alkyl acrylate ester monomers useful in the invention include straight-chain, cyclic, and branched-chain isomers of alkyl esters containing $C_1$–$C_{50}$ alkyl groups. Useful specific examples of alkyl acrylate esters include: methyl acrylate, ethyl acrylate, n-propyl acrylate, 2-butyl acrylate, iso-amyl acrylate, n-hexyl acrylate, heptyl acrylate, n-octyl acrylate, iso-octyl acrylate, 2-ethylhexyl acrylate, nonyl acrylate, decyl acrylate, undecyl acrylate, dodecyl acrylate, tridecyl acrylate, and tetradecyl acrylate.

When the chain transfer agent $L(SH)_m$ bears a functional group, a compound of Formula VIII (Scheme I) or Formula X (Scheme 2) may be further reacted with a functional aliphatic compound to form the linking group L and incorporate the R group into the compounds of Formulas I, II and V or VI. The nature of the functional groups on both the chain transfer agent and the aliphatic compounds are chosen so that they are reactive toward one another to form the L linking group. Examples of mutually reactive pairs include an acyl group (such as a carboxylic acid, acyl halide or ester) reacting with an alcohol or amine, an acyl or an amine reacting with a "leaving group" such as a halide or tosylate, and an isocyanate reacting with an alcohol or amine.

A compound of Formulas VIII or X may be provided with functional groups on the L linking group (in addition to the sulfhydryl group(s)) through the use of an appropriate functionalized chain-transfer agent $L(SH)_m$, wherein L contains a functional group. Suitable functional groups for inclusion in the chain-transfer agent include hydroxy, amino, halo, epoxy, haloformyl, aziridinyl, acid groups and salts thereof, which react with an electrophile or nucleophile, or are capable of further transformation into such groups. The use of a functionalized chain-transfer agent allows for subsequent incorporation of the "R" group of Formulas I and II, and V or VI. For example, the "L" group of the chain transfer agent may be substituted with an electrophilic ester moiety. This ester moiety will allow incorporation of a long chain "R" group by further reaction with an aliphatic alcohol having a nucleophilic hydroxyl group. Reaction between the two moieties produces an ester linkage, thereby linking the fluorochemical oligomeric moiety A with the aliphatic moiety R. Alternatively, for example, the L moiety may be substituted with a hydroxyl group that may be reacted with an aliphatic ester to link the fluorochemical oligomeric moiety A with the aliphatic moiety R.

Examples of such functionalized chain transfer agents include 2-mercaptoethanol, mercaptoacetic acid, 2-mercaptobenzimidazole, 2-mercaptobenzoic acid, 2-mercaptobenzothiazole, 2-mercaptobenzoxazole, 3-mercapto-2-butanol, 2-mercaptosulfonic acid, 2-mercaptonicotinic acid, 4-hydroxythiopheno-3-mercapto-1,2-propanediol, 1-mercapto-2-propanol, 2-mercaptopropionic acid, N-(2-mercaptopropionyl) glycine, 3-mercaptopropyltrimethoxysilane, 2-mercaptopyridine, 2-mercaptopyridine-N-oxide, 2-mercaptopyridinol, mercaptosuccinic acid, 2,3-mercaptopropanesulfonic acid, 2,3-dimercaptopropanol, 2,3-dimercaptosuccinic acid, cystine, cystine hydrochloride, cystine ethylester. Preferred functionalized chain-transfer agents include 2-mercaptoethanol, 3-mercapto-1,2-propanediol, 4-mercaptobutanol, 11-mercaptoundecanol, mercaptoacetic acid, 3-mercaptopropionic acid, 12-mercaptododecanoic acid, 2-mercaptoethylamine, 1-chloro-6-mercapto-4-oxahexan-2-ol, 2,3-dimercaptosuccinic acid, 2,3-dimercaptopropanol, 3-mercaptopropyltrimethoxysilane, 2-chloroethanethiol, 2-amino-3-mercaptopropionic acid, and compounds such as the adduct of 2-mercaptoethylamine and caprolactam.

Advantageously, the R group of Formulas I, II, V or VI may be incorporated by use of a non-functional chain transfer agents. Non-functionalized chain-transfer agents are those that contain a group capable of terminating a radical chain reaction (e.g., a sulfhydryl) but no further functional groups capable of reacting with nucleophiles, electrophiles, or capable of undergoing displacement reactions. In such cases, the aliphatic portion of $L(SH)_n$ provides the aliphatic group R of Formulas I, II and V or VI. Such compounds include mono, di, and polythiols such as ethanethiol, propanethiol, butanethiol, hexanethiol, n-octylthiol, t-dodecylthiol, 2-mercaptoethyl ether, 2-mercaptoimidazole, 2-mercaptoethylsulfide, 2-mercaptoimidazole, 8-mercaptomenthone, 2,5-dimercapto-1,3,4-thiadiazole, 3,4-toluenedithiol, o-, m-, and p-thiocresol, ethylcyclohexanedithiol, p-menthane-2,9-dithiol, 1,2-ethanedithiol, 2-mercaptopyrimidine, and the like. Longer chain alkyl thiols having 12 to 75 carbon atoms being preferred.

Whether functionalized or not, a chain transfer agent is present in an amount sufficient to control the number of polymerized monomer units in the oligomer. The end-capping agent is generally used in an amount of about 0.05 to about 0.5 equivalents, preferably about 0.25 equivalents, per equivalent of olefinic monomers VII and/or IX.

Also present in oligomerization process is a free-radical initiator as defined above in connection with X. Such compounds are known to those skilled in the art and include persulfates, azo compounds such as azoisobutyronitrile and azo-2-cyanovaleric acid and the like, hydroperoxides such as cumene, t-butyl, and t-amyl hydroperoxide, dialkyl peroxides such as di-t-butyl and dicumyl peroxide, peroxyesters such as t-butyl perbenzoate and di-t-butylperoxy phthalate, diacylperoxides such as benzoyl peroxide and lauroyl peroxide.

The initiating radical formed by an initiator can be incorporated into the fluorochemical oligomer to varying degrees depending on the type and amount of initiator used. A suitable amount of initiator depends on the particular initiator and other reactants being used. About 0.1 percent to about 5 percent, preferably about 0.1 percent, to about 0.8 percent, and most preferably about 0.2 percent to 0.5 percent by weight of an initiator can be used, based on the total weight of all other reactants in the reaction.

The oligomerization reaction of Schemes 1, 2 and 3 can be carried out in any solvent suitable for organic free-radical reactions. The reactants can be present in the solvent at any suitable concentration, e.g., from about 5 percent to about 90 percent by weight based on the total weight of the reaction mixture. Examples of suitable solvents include aliphatic and alicyclic hydrocarbons (e.g., hexane, heptane, cyclohexane), aromatic solvents (e.g., benzene, toluene, xylene), ethers (e.g., diethylether, glyme, diglyme, diisopropyl ether), esters (e.g., ethyl acetate, butyl acetate), alcohols (e.g., ethanol, isopropyl alcohol), ketones (e.g., acetone, methyl ethyl ketone, methyl isobutyl ketone), sulfoxides (e.g., dimethyl sulfoxide), amides (e.g., N,N-dimethylformamide, N,N-dimethylacetamide), halogenated solvents such as methylchloroform, FREON™ 113, trichloroethylene, $\alpha,\alpha,\alpha$,-trifluorotoluene, fluorinated ethers such as $C_4F_9OCH_3$ and the like, and mixtures thereof.

The oligomerization can be carried out at any temperature suitable for conducting an organic free-radical reaction. Particular temperature and solvents for use can be easily selected by those skilled in the art based on considerations such as the solubility of reagents, the temperature required for the use of a particular initiator, and the like. While it is not practical to enumerate a particular temperature suitable for all initiators and all solvents, generally suitable temperatures are between about 30° C. and about 200° C.

Useful fibrous substrates which may be topically treated (surface treated) include natural textiles and fabrics such as cotton or wool and synthetic fabrics or textiles such as polyester or nylon, as well as paper and leather. Topical treatment can be done via immersion, spray, foam, kiss roll and metering. For example, the substrate can be immersed in a dispersion or solution of the fluorochemical oligomer and agitated until it is saturated. The saturated substrate can then be run through a padder/roller to remove excess dispersion, dried in an oven at a relatively low temperature (e.g., 70° C.) for a time sufficient to remove the dispersion medium (e.g. solvents such as those used in the oligomerization reaction), and cured at a temperature and for a time sufficient to provide a cured treated substrate. This curing process can be carried out at temperatures between ambient temperature and about 150° C. depending on the particular composition used. In general, a temperature of about 40 to 150° C. for a period of about 10 minutes is suitable. The cured treated substrate can be cooled to room temperature and used as desired, e.g., incorporated or fashioned into a garment such as rainwear.

A fluorochemical oligomer in connection with the present invention is preferably used as an aqueous composition, in particular an aqueous dispersion in water. If the oligomer is made by solution polymerization, it can be dispersed in water, through vigorously mixing the solution oligomer with water. A solvent free dispersion can be obtained by subsequent distillation of the oligomerization solvent. In accordance with a preferred method of treating leather in connection with this invention, a leather such as a tanned hide is contacted with an aqueous composition, preferably an aqueous dispersion, comprising amphiphilic copolymer. Aqueous dispersions in accordance with the invention are suitable for the treatment of all conventional tanned hides, in particular hides tanned with mineral tanning agents, such as chromium(III), aluminum or zirconium salts. The tanned hides are usually neutralized before treatment, and may be dyed before treatment. However, dyeing may also be carried out after a waterproofing treatment in accordance with this invention.

The tanned hides can be treated with an aqueous dispersion comprising an oligomer in accordance with the invention preferably in an aqueous liquor obtained by diluting the oligomeric dispersions with water, at a pH of from 3 to 10, preferably from 5 to 8, and at from 20° C. to 70° C., preferably from 40° C. to 60° C. The amount of the oligomer dispersion applied to the leather in accordance with this invention is chosen so that sufficiently high or desirable water repellency is imparted to the substrate, said amount usually being between 0.1% and 30% by weight, preferably between 0.5% and 15% by weight, based on the shaved weight of the leather or the wet weight of the hide or wet blue leather. The amount which is sufficient to impart desired repellency can be determined empirically and can be increased as necessary or desired. The treatment is effected, for example, by drumming. After the treatment with the aqueous dispersion described above, the pH of the treatment liquor is preferably brought to 3–5, preferably 3.3–4, by addition of an acid in particular an organic acid, such as formic acid.

The amount of the fluorochemical composition applied to a substrate in accordance with this invention is chosen so that sufficiently high or desirable water and oil repellencies are imparted to the substrate surface, said amount usually being such that 0.01% to 5% by weight, preferably 0.05 to 2% by weight, of fluorine is present on the treated substrate. The amount which is sufficient to impart desired repellency can be determined empirically and can be increased as necessary or desired.

To prepare the aqueous dispersions, the oligomers, together with cationic or anionic and, if appropriate, nonionic dispersing and/or emulsifying or surfactant agents and, if appropriate, other auxiliaries and solvents, are vigorously dispersed in water, a relatively large amount of energy being supplied. To facilitate the preparation of the dispersion, the oligomer product may be dissolved first in solvent or mixture of solvents, and the dispersion is advantageously carried out in two separate steps, predispersion being carried out first, followed by fine dispersion. Predispersion can also be carried out by using high shearing forces, for example by using a high-speed stirrer, such as a dispersing machine of the Ultraturax™ type, and the predispersion thereby obtained is then subjected, for example, to ultrasonic treatment or treatment in a high pressure homogenizer. After this treatment, the particle size in the dispersion generally will be equal to or less than 1 (mu)m to the extent of more than 80%, preferably to the extent of more than 95%. Generally, the aqueous dispersion as a concentrate contains 5 to 50% by weight of an active composition (oligomers), 0.5 to 15% by weight of one or more dispersing and/or emulsifying agents, and 0 to 30% by weight of a solvent or solvent mixture, the remainder being water. Solventless dispersions can be prepared by removing the solvent by distillation.

Mixtures of water-insoluble solvents with water-soluble solvents can be employed as the solvent for preparation of the dispersion, the amount of the water-insoluble solvent in most cases being greater than the water-soluble solvent. Suitable water-soluble solvents are, for example, mono- or di-alcohols, lower ketones, polyglycol esters, and polyglycol ethers, or mixtures of such solvents. Examples of water-insoluble solvents are esters, ethers, and higher ketones. Low-boiling solvent portions can be removed by, for example, distillation, at a later time, if desired. Preferred water-insoluble solvents are esters or ketones, such as ethyl acetate, butyl acetate, and methyl ethyl ketone.

In order to increase repellency properties and the durability thereof and to aid in the application of an aqueous composition according to the present invention to a leather substrate to be treated therewith, it may be advantageous to incorporate into an aqueous composition according to this invention, one or more other substances such as oil and/or water repellent compositions and/or siloxane softening agents. Also other additives such as conventional leather finishing agents e.g. retanning, fatliquoring agents can be added.

Further suitable water and/or oil repellent composition that can be used in connection with this invention comprise polysiloxanes having fluoroaliphatic- and carboxyl-containing terminal groups as disclosed in WO 94/12561, fluoro- and polysiloxane- containing urethanes as disclosed in EP 298364, carboxyl group containing polysiloxanes as disclosed in EP 324345. Still further water and/or oil repellent compositions are disclosed in U.S. Pat. Nos. 4,525,305, 4,920,190, 4,782,175, 4,778,915, 4,539,006, 3,923,715 and 4,709,074.

This invention is illustrated by, but is not intended to be limited to, the following examples. Unless otherwise specified, all percentages shown in the examples and test methods which follow are percentages by weight.

EXAMPLES

Unless otherwise specified, all percentages shown in the examples and test methods which follow are percentages by weight.

Glossary

MeFBSE—$C_4F_9SO_2N(CH_3)CH_2CH_2OH$, can be prepared using the general procedure described in Example 3 of U.S. Pat. No. 2,803,656.

MeFOSE—$C_8F_{17}SO_2N(CH_3)CH_2CH_2OH$, can be prepared using the general procedure described in Example 3 of U.S. Pat. No. 2,803,656.

AC600—FLUOWET™ AC600, $C_6F_{13}C_2H_4OC(O)CH=CH_2$, available from Clariant GmbH, Germany.

MeFBSEMA—$C_4F_9SO_2N(CH_3)C_2H_4OC(O)C(CH_3)=CH_2$, can be prepared from MeFBSE and methacryloyl chloride (available from Aldrich Chemical Co.) using the general procedure described in U.S. Pat, No. 2,803,615.

MeFBSEA—$C_4F_9SO_2N(CH_3)CH_2CH_2OC(O)CH=CH_2$, can be prepared from MeFBSE and acryloyl chloride (available from Aldrich Chemical Co.) using the general procedure described in U.S. Pat. No. 2,803,615.

MeFOSEA—$C_8F_{17}SO_2N(CH_3)CH_2CH_2OC(O)CH=CH_2$, can be prepared from MeFOSE and acryloyl chloride using the general procedure described in U.S. Pat. No. 2,803,615.

FC-3573—SCOTCHGARD™ Leather Protector, 30% active solids emulsion containing a fluorochemical ester, available from 3M Company, St. Paul, Minn.

$C_{18}H_{37}OH$—1-octadecanol, available from Aldrich Chemical Co.

$C_{17}H_{35}COOH$—stearic acid, available from Aldrich Chemical Co.

$C_{21}H_{43}COOH$—behenic (docosenoic) acid, available from Aldrich Chemical Co.

UNILIN™ 700—polyethylene 700 alcohol (having around 50 carbon atoms), available from Baker Petrolite Corp., Tulsa, Okla.

UNICID™ 700—polyethylene 700 acid (having around 50 carbon atoms), available from Petrolite Corp., St. Louis, Mo.

EMPOL™ 1008—distilled and hydrogenated dimer acid made from oleic acid, having an acid equivalent weight of 305 as determined by titration, available from Henkel Corp./Emery Group, Cincinnati, Ohio. ODA—octadecyl acrylate, $C_{18}H_{37}OC(O)CH=CH_2$, available from Aldrich Chemical Co.

UNILIN™ 700A—To a three necked round bottom flask equipped with a mechanical stirrer and a Dean-Stark apparatus was added 200 g (0.231 mol) of UNLTIN™ 700, 16.7 g (0.231 mol) of acrylic acid, 2 g of methanesulfonic acid and 400 mL of toluene. The resulting mixture was heated to reflux for approximately 15 hours, during which time water had collected in the Dean-Stark apparatus. IR of the reaction product showed no —COOH and —OH peaks, indicating that the ester formation was complete. To the hot ester solution was slowly added 10 g of $Ca(OH)_2$ while stirring and then hot filtered. The resulting mixture was filtered hot, the toluene was removed from the filtrate by heating under reduced pressure, and the remaining wet solid was dried in a vacuum oven. Also available as X-8503™ from Baker-Petrolite, Tulsa, Okla.

methyl 3-mercaptopropionate—$HSCH_2CH_2COOCH_3$, available from Aldrich Chemical Co.

2-mercaptoethanol—$HSCH_2CH_2OH$, available from Aldrich Chemical Co.

3-mercapto-1,2-propanediol—$HSCH_2CH(OH)CH_2OH$, available from Aldrich Chemical Co.

AIBN—2,2'-azobisisobutyronitrile, available as VAZO™ 64 initiator from E. I. duPont de Nemours & Co., Wilmington, Del.

VAZO 88™ —1,1'-azobiscyclohexylnitrile initiator from E. I. duPont de Nemours & Co., Wilmington, Del.

Preparation of Fluorochemical Compounds and Intermediates $(MeFBSEA)_4$-S—$CH_2CH_2OH$—To a round bottom flask equipped with stirrer, thermometer, reflux condenser and nitrogen bubbler was added 1695 g (4.124 mol) of MeFBSEA monomer and 1500 g of ethyl acetate, and nitrogen was bubbled through the resulting solution for a period of 15 minutes. To the solution was then added 80.6 g (1.031 mol) of 2-mercaptoethanol, and nitrogen was bubbled for an additional 2 minutes. AIBN initiator (0.5 wt %) was added and the resulting mixture heated to 65° C. for approximately 15 hours under nitrogen atmosphere. IR analysis of the resulting oligomer showed the absence of a >C=C< peak at 1637 cm$^{-1}$ indicating no residual monomer. The ethyl acetate was evaporated under vacuum to give the desired oligomeric alcohol., $(MeFBSEMA)_4$-S—$CH_2CH_2OH$—To a round bottom flask equipped with stirrer, thermometer, reflux condenser and nitrogen bubbler was added 501 g (1.179 mol) of MeFBSEMA and 500 mL of ethyl acetate. The contents of the flask were stirred to form a solution, and nitrogen was bubbled through the solution for 15 minutes. To this solution was then added 23.03 g (0.295 mol) of 2-mercaptoethanol, and nitrogen was bubbled through the contents of the flask for an additional 2 minutes. 0.5% by weight of AIBN was added and the resulting mixture heated to 65° C. for approximately 15 hours under a nitrogen atmosphere. IR spectra of this material showed the absence of a >C=C< peak at 1637 cm$^{-1}$, indicating no residual monomer present. The polymer solution was poured in hexanes, causing the polymer to precipitate as a viscous liquid, which was removed by decantation and dried under vacuum.

$(AC600)_4$-S—$CH_2CH_2OH$—Essentially the same procedure was followed as for preparing $(MeFBSEA)_4$-S—$CH_2CH_2OH$ except that the MeFBSEA was replaced with an equimolar amount of AC600.

$(MeFOSEA)_4$-S—$CH_2CH(OH)CH_2OH$—To a round bottom flask equipped with stirrer, thermometer, reflux condenser and nitrogen bubbler was added 400 g (0.655 mol) of MeFOSEA and 400 mL of ethyl acetate. While stirring, nitrogen was bubbled through the resulting solution for 15 minutes. To this solution was added 17.7 g (0. 164 mol) of 3-mercapto-1,2-propanediol, and bubbling with nitrogen was continued for another 2 minutes. 0.5% (wt) of AIBN was added and the mixture was heated to 65° C. for about 15 hours under a nitrogen atmosphere. IR spectra of this material showed the absence of >C=C< peak at 1637 cm$^{-1}$, indicating no residual monomer. This mixture was poured in $CH_3OH$ and the resulting white powder was filtered and dried under vacuum.

$(MeFBSEMA)_4$-S—$CH_2CH(OH)CH_2OH$—Essentially the same procedure was followed as for preparing $(MeFOSEA)_4$-S—$CH_2CH(OH)CH_2OH$ except that the MeFOSEA was replaced with an equimolar amount of MeFBSEMA.

$(MeFBSEA)_4$-S—$CH_2CH(OH)CH_2OH$—Essentially the same procedure was followed as for preparing $(MeFOSEA)_4$-S—$CH_2CH(OH)CH_2OH$ except that the MeFOSEA was replaced with an equimolar amount of MeFBSEA.

$(MeFBSEMA)_4$-S—$CH_2CH(OH)CH_2OH$—Essentially the same procedure was followed as for preparing $(MeFOSEA)_4$-S—$CH_2CH(OH)CH_2OH$ except that the MeFOSEA was replaced with an equimolar amount of MeFBSEMA. $(MeFBSEA)_4$-S—$CH_2CH_2OOCC_{17}H_{35}$—To a three necked round bottom flask equipped with a mechanical stirrer and a dean-stark apparatus was added 150 g (0.0871 mol) of $(MeFBSEA)_4$-S—$CH_2CH_2OH$, 24.8 g (0.0871 mol) of stearic acid, 1% of p-toluene sulfonic acid (based on solids) and 200 mL of toluene. The resulting mixture was then heated to reflux for approximately 15 hours, with 1.6 mL of water collecting in the dean-stark apparatus. IR analysis of the reaction product showed no residual —COOH and —OH peaks, indicating complete esterification. To the hot reaction product was slowly added 10 g of $Ca(OH)_2$ while stirring, then the mixture was filtered to remove the solids. The toluene was removed from the filtrate using rotary evaporation and the resulting solid was dried in a vacuum oven.

Emulsification Procedure: 100 g of the above material was dissolved in 100 g of hot ethyl acetate. To this solution while stirring was added a mixture of 400 g of deionized water and 5 g of SIPONATE™ DS-10 (sodium dodecylbenzenesulfonate, available from Rhone-Poulenc, Inc, Cranbury, N.J.), with the mixture heated to 70° C. While stirring, the resulting mixture was sonicated for 6 minutes, then 24 g of ethylene glycol was mixed in. The ethyl acetate was evaporated under vacuum to provide a stable emulsion having 19.3% solids.

$(MeFBSEMA)_4$-S—$CH_2CH_2OOCC_{17}H_{35}$—This ester was prepared using essentially the same procedure as described for preparing $(MeFBSEA)_4$-S—$CH_2CH_2OOCC_{17}H_{35}$, except that the $(MeFBSEA)_4$-S—$CH_2CH_2OH$ was replaced with an equimolar amount of $(MeFBSEMA)_4$-S—$CH_2CH_2OH$. Also, the same emulsification procedure was followed (to give an 18.5% solids emulsion).

$(AC600)_4$-S—$CH_2CH_2OOCC_{17}H_{35}$—This ester was prepared using essentially the same procedure as described for preparing $(MeFBSEA)_4$-S—$CH_2CH_2OOCC_{17}H_{35}$, except that the $(MeFBSEA)_4$-S—$CH_2CH_2OH$ was replaced with an equimolar amount of $(AC600)_4$-S—$CH_2CH_2OH$.

$(MeFBSEA)_4$-S—$CH_2CH_2OOCC_{21}H_{43}$—This ester was prepared using essentially the same procedure as described for preparing $(MeFBSEA)_4$-S—$CH_2CH_2OOCC_{17}H_{35}$, except that the $C_{17}H_{35}COOH$ was replaced with an equimolar amount of $C_{21}H_{43}COOH$.

$(MeFBSEMA)_4$-S—$CH_2CH_2OOCC_{21}H_{43}$—This ester was prepared using essentially the same procedure as described for preparing (MeFBSEA)$_4$-S—CH$_2$CH$_2$OOCC$_{17}$H$_{35}$, except that the C$_{17}$H$_{35}$COOH was replaced with an equimolar amount of C$_{21}$H$_{43}$COOH and the (MeFBSEA)$_4$-S—CH$_2$CH$_2$OH was replaced with an equimolar amount of (MeFBSEMA)$_4$-S—CH$_2$CH$_2$OH.

(MeFBSEA)$_4$-S—CH$_2$CH$_2$OOC-UNICID™ 700—This ester was prepared using essentially the same procedure as described for preparing (MeFBSEA)$_4$-S—CH$_2$CH$_2$OOCC$_{17}$H$_{35}$, except that the C$_{17}$H$_{35}$COOH was replaced with an equimolar amount of UNICID™ 700.

(MeFBSEMA)$_4$-S—CH$_2$CH$_2$OOC-UNICID™ 700—This ester was prepared using essentially the same procedure as described for preparing (MeFBSEA)$_4$-S—CH$_2$CH$_2$OOCC$_{17}$H$_{35}$, except that the C$_{17}$H$_{35}$COOH was replaced with an equimolar amount of UNICID™ 700 and the (MeFBSEA)$_4$-S—CH$_2$CH$_2$OH was replaced with an equimolar amount of (MeFBSEMA)$_4$-S/CH$_2$CH$_2$OH.

(MeFOSEA)$_4$-S—CH$_2$CH(OOCC$_{17}$H$_{35}$)CH$_2$OOCC$_{17}$H$_{35}$—To a 3-necked round bottom flask equipped with a mechanical stirrer and Dean-Stark apparatus was added 50 g (0.0196 mol) of (MeFOSEA)$_4$-S—CH$_2$CH(OH)CH$_2$OH, 11.2 g (0.0392 mol) of stearic acid, 0.5 mL of methanesulfonic acid and 100 mL of toluene. The resulting mixture was heated to reflux for approximately 15 hours, during which time some water had collected in the Dean-Stark apparatus. IR spectra of this mixture showed no —COOH or —OH peaks. To this hot mixture 10 g of Ca(OH)$_2$ was added slowly with stirring, and the hot solution was filtered. Toluene was removed from the filtrate by heating under reduced pressure, and the remaining solids were dried in a vacuum oven.

(MeFBSEA)$_4$-S—CH$_2$CH(OOCC$_{17}$H$_{35}$)CH$_2$OOCC$_{17}$H$_{35}$—This ester was prepared using essentially the same procedure as described for preparing (MeFOSEA)$_4$-S—CH$_2$CH(OOCC$_{17}$H$_{35}$)CH$_2$OOCC$_{17}$H$_{35}$, except that the (MeFOSEA)$_4$-S—CH$_2$CH(OH)CH$_2$OH was replaced with an equimolar amount of (MeFBSEA)$_4$-S—CH$_2$CH(OH)CH$_2$OH.

(MeFBSEMA)$_4$-S—CH$_2$CH(OOCC$_{17}$H$_{35}$)CH$_2$OOCC$_{17}$H$_{35}$—This ester was prepared using essentially the same procedure as described for preparing (MeFOSEA)$_4$-S—CH$_2$CH(OOCC$_{17}$H$_{35}$)CH$_2$OOCC$_{17}$H$_{35}$, except that the (MeFOSEA)$_4$-S—CH$_2$CH(OH)CH$_2$OH was replaced with an equimolar amount of (MeFBSEMA)$_4$-S—CH$_2$CH(OH)CH$_2$OH.

2MeFOSE-EMPOL™ 1008—To a 500 mL 2-necked round-bottom flask equipped with overhead condenser, thermometer and Dean-Stark trap wrapped with heat tape was charged 57.8 g (0.190 eq) of Empol™ 1008 dimer acid, 100 g (0.185 eq) of MeFOSE, 1 g of p-toluenesulfonic acid and 50 g of toluene. The resulting mixture was placed in an oil bath heated to 150° C. The degree of esterification was monitored by measuring the amount of water collected in the Dean-Stark trap and also by using gas chromatography to determine the amount of unreacted fluorochemical alcohol. After 18 hours of reaction, about 2.8 mL of water was collected and a negligible amount of fluorochemical alcohol remained, indicating a complete reaction. The reaction mixture was then cooled to 100° C. and was twice washed with 120 g aliquots of deionized water to a water pH of 3. The final wash was removed from the flask by suction, and the reaction mixture was heated to 120° C. at an absolute pressure of about 90 torr to remove volatiles. The product, a brownish solid, was characterized as containing the desired product by $^1$H and $^{13}$C NMR spectroscopy and thermogravimetric analysis.

[(MeFBSEA)$_4$-S—CH$_2$CH$_2$OOC]$_2$-EMPOL™ 1008—This ester was prepared using essentially the same procedure as described for preparing 2MeFOSE-EMPOL™ 1008, except that the MeFOSE was replaced with an equimolar amount of (MeFBSEA)$_4$-S—CH$_2$CH$_2$OH.

MeFBSEMA/UNILIN™ 700A/HSCH$_2$CH$_2$COOCH$_3$ Copolymer (low molecular weight—To a round bottom flask equipped with stirrer, thermometer, reflux condenser and nitrogen bubbler was added 42.5 g (0.1 mol) of MeFBSEMA, 70 g of methyl isobutyl ketone, 18.8 g (0.025 mol) of UNILIN™ 700A (X-8503) and 3 g (0.025 mol) of methyl 3-mercaptopropionate. This mixture was heated to 100° C. to obtain a homogenous solution. While stirring, nitrogen was bubbled through the resulting solution for 2 minutes. To this solution was added 0.25 g of VAZO™ 88 and the resulting mixture was heated to 98–100° C. for about 15 hours under a nitrogen atmosphere with stirring. IR spectra of this material showed the absence of a >C=C< peak at 1637 cm$^{-1}$, indicating no residual monomer. The solvent was evaporated under vacuum to recover the solid product.

MeFBSEMA/UNILIN™ 700A Copolymer (high molecular weight)—To a round bottom flask equipped with stirrer, thermometer, reflux condenser and nitrogen bubbler was added 42.5 g (0.1 mol) of MeFBSEMA, 70 g of methyl isobutyl ketone and 18.8 g (0.025 mol) of UNSILIN™ 700A (X-8503). This mixture was heated to 100° C. until a homogenous solution was obtained. While stirring, nitrogen was bubbled through the resulting solution for 2 minutes. To this solution was added 0.25 g of VASO™ 88, and the resulting mixture was heated to 98–100° C. for about 15 hours under a nitrogen atmosphere. IR spectra of this material showed the absence of >C=C< peak at 1637 cm$^{-1}$, indicating no residual monomer. The solvent was evaporated under vacuum to recover the solid product.

MeFBSEMA/ODA/HSCH$_2$CH$_2$COOCH$_3$ Copolymer—To a round bottom flask equipped with stirrer, thermometer, reflux condenser and nitrogen bubbler was added 42.5 g (0.1 mol) of MeFBSEMA, 60 g of ethyl acetate, 8.1 g (0.025 mol) of ODA and 3 g (0.025 mol) of methyl 3-mercaptopropionate. While stirring, nitrogen was bubbled through the resulting solution for 5 minutes. To this solution was added 0.25 g of AIBN and the resulting mixture was heated to 65° C. for about 15 hours under a nitrogen atmosphere. IR spectra of this material showed the absence of >C=C< peak at 1637 cm$^{-1}$, indicating no residual monomer. The solvent was evaporated under vacuum to recover the solid product.

MeFOSE-UNICID™ 700—To a 1000 mL 3-necked round-bottom flask equipped with overhead condenser, thermometer and Dean-Stark trap wrapped with heat tape was charged 135 g (0.2424 mol) of MeFOSE, 215.7 g (0.2424 mol) of UNICID™ 700, 3.5 g of p-toluenesulfonic acid and 500 mL of toluene. The resulting mixture was then heated to reflux for approximately 15 hours. IR analysis of the reaction product showed no residual —COOH and —OH peaks, indicating complete esterification. To the hot reaction product was slowly added 10 g of Ca(OH)$_2$ while stirring, then the mixture was filtered to remove the solids. The toluene was removed from the filtrate using rotary evaporation and the resulting solid was dried in a vacuum oven.

Test Methods

Water Repellency (WR)—The water repellency of a treated substrate is measured using the following test. In this test, samples are challenged to penetrations by blends of deionized water and isopropyl alcohol (IPA). Each blend is assigned a rating number as shown below:

| Water Repellency Rating Number | Water/IPA Blend (% by volume) |
| --- | --- |
| 0 | 100% water |
| 1 | 90/10 water/IPA |
| 2 | 80/20 water/IPA |
| 3 | 70/30 water/IPA |
| 4 | 60/40 water/IPA |
| 5 | 50/50 water/IPA |
| 6 | 40/60 water/IPA |
| 7 | 30/70 water/IPA |
| 8 | 20/80 water/IPA |
| 9 | 10/90 water/IPA |
| 10 | 100% IPA |

In running the Water Repellency Test, a treated substrate is placed on a flat, horizontal surface. Five small drops of water or a water/IPA mixture are gently placed at points at least two inches apart on the sample. If, after observing for 15 seconds at a 45° angle, four of the five drops are visible as a sphere or a hemisphere, the nonwoven web sample is deemed to pass the test. The reported water repellency rating corresponds to the highest numbered water or water/IPA mixture for which the nonwoven sample passes the described test.

It is desirable to have a water repellency rating of at least 3.

Oil Repellency (OR)—The oil repellency of a treated substrate is measured using the following test. In this test, samples are challenged to penetration by oil or oil mixtures of varying surface tensions. Oils and oil mixtures are given a rating corresponding to the following:

| Oil Repellency Rating Number | Oil Composition |
| --- | --- |
| 0 | (fails Kaydol ™ mineral oil) |
| 1 | Kaydol ™ mineral oil |
| 2 | 65/35 (vol) mineral oil/n-hexadecane |
| 3 | n-hexadecane |
| 4 | n-tetradecane |
| 5 | n-dodecane |
| 6 | n-decane |
| 7 | n-octane |
| 8 | n-heptane |

The Oil Repellency Test is run in the same manner as is the Water Repellency Test, with the reported oil repellency rating corresponding to the highest oil or oil mixture for which the nonwoven web sample passes the test.

It is desirable to have an oil repellency rating of at least 1, preferably a rating of at least 3.

Abraded Oil and Water Repellency—The repellency of an abraded treated substrate was measured on 5 cm×12.5 cm test pieces of treated substrate which had been abraded using 10 back-and-forth rubs over a 5-second period with abrasive paper ("WETORDRY-TRI-M-ITE" No. 600C) in an AATCC crockmeter (Model CM-1). The above-described OR and WR repellency tests were performed on the abraded test pieces and the repellency ratings recorded as Abraded Oil Repellency (AOR) and Abraded Water Repellency (AWR) values.

Spray Rating.(SR)—The spray rating of a treated substrate is a value indicative of the dynamic repellency of the treated substrate to water that impinges on the treated substrate. The repellency is measured by Standard Test Number 22, published in the 1985 Technical Manual and Yearbook of the American Association of Textile Chemists and Colorists (AATCC), and is expressed in terms of "spray rating" of the tested substrate. The spray rating is obtained by spraying 250 mL water on the substrate from a distance of 15 cm. The wetting pattern is visually rated, using a 0 to 100 scale, where 0 means complete wetting and 100 means no wetting at all.

Contact Angle Test Procedure—The following procedure was used to measure both advancing and receding contact angles.

A sample of clean or nylon film is cut into 85 mm×13 mm rectangular strips. Each strip is cleaned by dipping the strip in and out of methyl alcohol, wiping the strip with a Kimwipe™ wiper (commercially available from Kimberly-Clark Corp., Boswell, Ga.), taking care not to hand-touch the strip's surface, and allowing the strip to dry for 15 minutes. Then, using a small binder clip to hold one end of the strip, the strip is immersed in a treating solution consisting of a 3% (wt) solution of the alkylated fluorochemical oligomer compound in either 50/50 (wt) $\alpha,\alpha,\alpha$-trifluorotoluene/toluene, methyl isobutyl ketone, ethyl acetate or 50/50 (wt) ethylacetate/toluene (or mixtures thereof) and the strip is then withdrawn slowly and smoothly from the solution. The coated film strip is tilted to allow any solution run-off to accumulate at the corner of the strip, and a Kimwipe™ tissue is touched to the corner to pull away the solution buildup. The coated film strip is allowed to air dry in a protected location for a minimum of 30 minutes and then is baked for 10 minutes at 150° C. to dry and cure the coating.

After the treatment is dry and cured, the advancing or receding contact angles of water and n-hexadecane are measured using a CAHN Dynamic Contact Angle Analyzer, Model DCA 322 (a Wilhelmy balance apparatus equipped with a computer for control and data processing, available from ATI, Madison, Wis.) using the following procedure. The CAHN Dynamic Contact Angle Analyzer is calibrated using a 500 mg weight. An alligator clip is fastened to a piece of coated film strip about 30 mm long, and the clip and film piece are hung from the stirrup of the balance. A 30 mL glass beaker containing approximately 25 mL of n-hexadecane is placed under the balance stirrup, and the beaker is positioned so that the coated film strip is centered over the beaker and its contents but not touching the walls of the beaker. Using the lever on the left side of the apparatus, the platform supporting the beaker is carefully raised until the surface of the test liquid is 2–3 mm from the lower edge of the film strip. The door to the apparatus is closed, the "Configure" option is chosen from the "Initialize" menu of the computer, the "Automatic" option is chosen from the "Experiment" menu, and the computer program then calculates the time for a total of 3 scans. The result should be a time interval of 1 second and estimated total time of 5 minutes, which are the acceptable settings to show the baseline weight of the sample. The Return Key is then pressed to begin the automatic measurement cycle. 10 readings of the baseline are taken before the scan begins. The apparatus then raises and lowers the liquid so that 3 scans are taken. The "Least Squares" option is then selected from the "Analysis" menu, and the average advancing or receding contact angle is calculated from the 3 scans of the film sample. The 95% confidence interval for the average of the 3 scans is typically about ±1.2°.

Bally Penetrometer Test—For the testing of shoe upper leathers for dynamic water repellency, a Bally Penetrometer test was utilized according to test procedure DIN 53338. For this test, a Bally Penetrometer Model 5023 (a standardized dynamic testing machine for shoe upper leather) was used. To simulate an upper leather in actual use, the test piece was alternatively buckled and stretched by the machine while in contact with water on one side. The values measured in this test are:

(1) the time elapsed until water first penetrates from one side of the test piece of treated leather to the other (for untreated leather, said time is typically less than 15 minutes), and (2) the weight percent increase of the test piece caused by water absorption during the test (for untreated leather, said weight increase is typically greater than 100% after one hour).

The test was run for a total of 6 hours, after which the percent water pickup was measured.

Dynamic Saline Water Resistant Test (Maeser Flexes)—The water resistance of the leathers was tested according to ASTM D-2009-70, using a Maeser water penetration tester. The number of Maeser flexes required to induce water penetration into the leather was recorded. Since this test utilizes saline water, it is useful for predicting the resistance of leather to damage not only from water but also from perspiration.

Examples 1–9 and Comparative Examples C1–C5

In this series of experiments, candidate repellents were each dissolved at 3% in either ethyl acetate, methyl isobutyl ketone or toluene or mixtures thereof Then each resulting treating solution was applied to samples of (1) cowhide nubuck leather (Timberland's "Water Wheat Buck" cowhide nubuck leather, 1.6 mm, for footwear in crust condition, chrome tanned and dried, containing a hydrophobic fatliquor) and (2) grain leather, (similar to white athletic shoe leather). Application was done using a paint brush, until each surface was completely painted but not painted to the point of saturation (i.e., no free liquid was standing). Each treated leather sample was then allow to dry at room temperature, then the sample was tested for water repellency (WR) and oil repellency (OR).

In Examples 1–9, various alkylated fluorochemical oligomers of this invention were evaluated. Each fluorochemical oligomer contained perfluorobutyl-terminated pendent groups ($R_f$) except for the oligomer in Example 8, which contained perfluorooctyl-terminated pendent groups. The aliphatic moiety (R) was varied from 17 to 50 carbon atoms, and the linking group (L) in each case contained an ester group.

In Comparative Examples C1–C3, copolymers of fluorochemical (meth)acrylates and long chain hydrocarbon acrylates having fluorine-free aliphatic groups (R&) containing either 18 or 50 carbon atoms were evaluated.

In Comparative Examples C4–C5, esters of MeFOSE alcohol and long chain fatty acids were evaluated. Comparative Example C5 represents a fluoroaliphatic dimer acid derivative described as a useful leather repellent in European Patent EP 613462.

Results are presented in TABLE 1.

TABLE 1

| | Repellent | WR | | OR | |
|---|---|---|---|---|---|
| Ex. | Composition | Nubuck | Grain | Nubuck | Grain |
| 1 | (MeFBSEA)$_4$—S—CH$_2$CH$_2$OOCC$_{17}$H$_{35}$ | 9 | 8 | 7 | 5 |
| 2 | (MeFBSEMA)$_4$—S—CH$_2$CH$_2$OOCC$_{17}$H$_{35}$ | 9 | 6 | 6 | 6 |
| 3 | (MeFBSEA)$_4$—S—CH$_2$CH$_2$OOCC$_{21}$H$_{43}$ | 9 | 8 | 6 | 5 |
| 4 | (MeFBSEMA)$_4$—S—CH$_2$CH$_2$OOCC$_{21}$H$_{43}$ | 7 | 7 | 5 | 5 |
| 5 | (MeFBSEA)$_4$—S—CH$_2$CH$_2$OOC-UNICID ™ 700 | 4 | 2 | — | — |
| 6 | (MeFBSEMA)$_4$—S—CH$_2$CH$_2$OOC-UNICID ™ 700 | 5 | 3 | 5 | 5 |
| 7 | (MeFBSEMA)$_4$—S—CH$_2$CH(OOCC$_{17}$H$_{35}$)CH$_2$OOCC$_{17}$H$_{35}$ | 8 | 9 | 5 | 6 |
| 8 | (MeFOSEA)$_4$—S—CH$_2$CH(OOCC$_{17}$H$_{35}$)CH$_2$OOCC$_{17}$H$_{35}$ | 4 | 3 | 6 | 6 |
| 9 | [(MeFBSEA)$_4$—S—CH$_2$CH$_2$OOC]$_2$-EMPOL ™ 1008 | 9 | 8 | 7 | 5 |
| C1 | MeFBSEMA/UNILIN ™ 700A/HSCH$_2$CH$_2$COOCH$_3$ (low MW copol.) | 2 | 2 | 3 | 2 |
| C2 | MeFBSEMA/UNILIN ™ 700A (high MW copol.) | 4 | 3 | 0 | 0 |
| C3 | MeFBSEMA/ODA/HSCH$_2$CH$_2$COOCH$_3$ | 8 | 6 | 3 | 3 |
| C4 | MeFOSE-UNICID ™ 700 | 7 | 7 | 2 | 2 |
| C5 | 2MeFOSE-EMPOL ™ 1008 | 9 | 9 | 6 | 6 |

The data in TABLE 1 show that, in general, the alkylated fluorochemical oligomers of this invention impart comparable or superior water and oil repellency to leather as compared to the comparative treatments. This is accomplished even though the pendent fluoroaliphatic groups in nearly all of the alkylated fluorochemical oligomers contain only four carbon atoms. Comparative Examples C1–C3 show that generally inferior oil repellency results when the long chain alkyl group is copolymerized with the fluorochemical rather than post-reacted to form a linking group with the fluorochemical oligomer. Comparative Example C4 shows that relatively poor oil performance is attained when a single alkyl chain perfluorooctyl group-containing alcohol is reacted with a long chain acid. In general, oil and water repellency imparted to leather by the alkylated fluorochemical oligomers of this invention is comparable to the that imparted by the leather treatment of Comparative Example C5 (described in European Patent EP 613462).

Also, advancing contact angles (ACA) and receding contact angles (RCA) in degrees were measured for each treated nylon film sample using both deionized water (DIW) and n-hexadecane (n-HD). In this series, $(AC600)_4$-S—$CH_2CH_2OOCC_{17}H_{35}$ was included as Example 10.

Contact angle results are presented in TABLE 2.

TABLE 2

| Ex. | Repellent Composition | DIW ACA | DIW RCA | n-HD: ACA | n-HD: RCA |
|---|---|---|---|---|---|
| 1 | $(MeFBSEA)_4$—S—$CH_2CH_2OOCC_{17}H_{35}$ | 112 | 82 | 81 | 37 |
| 2 | $(MeFBSEMA)_4$—S—$CH_2CH_2OOCC_{17}H_{35}$ | 124 | 87 | 74 | 42 |
| 3 | $(MeFBSEA)_4$—S—$CH_2CH_2OOCC_{21}H_{43}$ | 108 | 71 | 80 | 12 |
| 4 | $(MeFBSEMA)_4$—S—$CH_2CH_2OOCC_{21}H_{43}$ | 111 | 75 | 77 | 45 |
| 5 | $(MeFBSEA)_4$—S—$CH_2CH_2OOC$-UNICID™ 700 | 137 | 79 | 90 | 24 |
| 6 | $(MeFBSEMA)_4$—S—$CH_2CH_2OOC$-UNICID™ 700 | 126 | 64 | 80 | 45 |
| 7 | $(MeFBSEMA)_4$—S—$CH_2CH(OOCC_{17}H_{35})CH_2OOCC_{17}H_{35}$ | 122 | 70 | 78 | 6 |
| 8 | $(MeFOSEA)_4$—S—$CH_2CH(OOCC_{17}H_{35})CH_2OOCC_{17}H_{35}$ | 120 | 103 | 79 | 73 |
| 9 | $[(MeFBSEA)_4$—S—$CH_2CH_2OOC]_2$-EMPOL™ 1008 | 102 | 64 | 89 | 14 |
| 10 | $(AC600)_4$—S—$CH_2CH_2OOCC_{17}H_{35}$ | 108 | 69 | 87 | 48 |
| C1 | MeFBSEMA/UNILIN™ 700A/$HSCH_2CH_2COOCH_3$ (low MW copol.) | 123 | 74 | 77 | 30 |
| C2 | MeFBSEMA/UNILIN™ 700A (high MW copol.) | 120 | 80 | 74 | 50 |
| C3 | MeFBSEMA/ODA/$HSCH_2CH_2COOCH_3$ | 123 | 81 | 77 | 8 |
| C4 | MeFOSE-UNICID™ 700 | 131 | 103 | 87 | 63 |
| C5 | 2MeFOSE-EMPOL™ 1008 | 119 | 66 | 75 | 0 |

The data in TABLE 2 show that, in general, the alkylated fluorochemical oligomers of this invention impart comparable or superior advancing and receding contact angles as compared to the comparative treatments. Again, this is accomplished even through the pendent fluoroaliphatic groups in most of the alkylated fluorochemical oligomers contain only four carbon atoms. Due to their high receding contact angles against n-hexadecane, one would expect several of the alkylated fluorochemical oligomers to show excellent anti-staining performance, especially the oligomer of Example 8 which exhibits a 73° receding contact angle vs. n-hexadecane. The treatment used in Compative Example C5 has susceptibility to soiling, as is predicted by the n-hexadecane receding contact angle value of zero.

Examples 11–14 and Comparative Examples C6–C7

Three fluorochemical repellent candidates were evaluated as leather treatments in a series of lab experiments designed to simulate field trials: $(MeFBSEA)_4$-S—$CH_2CH_2OOCC_{17}H_{35}$, $(MeFBSEMA)_4$-S—$CH_2CH_2OOCC_{17}H_{35}$ (both alkylated fluorochemical oligomers of this invention) and FC-3573, a commercial fluorochemical leather treatment. The leather used in this series of experiments was cowhide nubuck for shoe upper in crust condition, 1.6 mm (available from Incusa Tannery, Valencia, Spain). All wet processing was done via exhaustion using 33 cm diameter drums (Sandoz System, available from Werner Mathis AG, Switzerland), using 100 g of small leather samples for each experiment. All percentages of ingredients given below are based on the leather weight. For $(MeFBSEA)_4$-S—$CH_2CH_2OOCC_{17}H_{35}$, $(MeFBSEMA)_4$-S—$CH_2CH_2OOCC_{17}H_{35}$ and FC-3573, the designated % of fluorochemical emulsion used was 7.8%, 8% and 5% respectively.

In Examples 11–12 and Comparative Example C6, each fluorochemical emulsion was "pasted" with the fatliquor. Prior to treatment with the oligomer emulsion/fatliquor blend, the leather was processed as follows: (1) re-wet with 800% water at 40° C. for 50 minutes, then drained of water, (2) neutralized using a mixture of 500% water and 2% sodium formate at 40° C. for 20 minutes, followed by addition of 1.75% sodium bicarbonate for an additional 40 minutes, then drained, (3) then dyed with a mixture of 400% water, 2.5% LUGANIL™ Brown NGB (available from BASF Corp., Germany) and 2% mimosa tannin at 35° C. for 60 minutes, followed by addition of 0.75% formic acid for an additional 20 minutes, then drained. The pasting was done with 500% water at 50° C. to which was added 9% EUPILON™ IN (available from TFL) and the designated % of fluorochemical emulsion at 50° C. for 60 minutes, followed by addition of 0.75% formic acid for an additional 20 minutes, and then draining. The pasted leather was then chrome capped using a mixture of 500% water and 2.5% CHROMITAN™ B (available from BASF Corp.) at 40° C. for 50 minutes, followed by draining, washing and drying.

In Examples 13–14 and Comparative Example C7, each fluorochemical emulsion was applied to nubuck leather via a "new bath" exhaustion procedure subsequent to a comparable re-wetting, neutralization, dyeing and fatliquoring process as described for pasting. In each case, $(MeFBSEA)_4$-S—$CH_2CH_2OOCC_{17}H_{35}$ was run at 7.8%., fluorochemical emulsion concentration, $(MeFBSEMA)_4$-S—$CH_2CH_2OOCC_{17}H_{35}$ was run at 8% concentration and FC-3573 was run at 5% concentration, each concentration based on the weight of leather charged to the drum. The emulsion concentrations were chosen so that all three fluorochemical repellents were evaluated on the same percent solids basis, based on the weight of the leather.

For the new bath, the following procedure was used: (1) mixture of 500% water and designated % fluorochemical emulsion at 40° C. for 45 minutes, (2) 0.3% formic acid for 15 minutes, (3) add 2.5% Cromitan™ B for 50 minutes, then drained.

Each dried treated leather sample was then evaluated for water repellency and oil repellency (WR, OR), initially and after abrasion by sandpaper (AWR, AOR), and also a spray rating (SR) was determined.

Results from these field trials are presented in TABLE 3.

TABLE 3

| Ex. | Repellent Composition | Appl. | WR | AWR | OR | AOR | SR |
|---|---|---|---|---|---|---|---|
| 11 | $(MeFBSEA)_4$—S—$CH_2CH_2OOCC_{17}H_{35}$ | pasted | 6 | 5 | 1–5* | 0+ | 80 |
| 12 | $(MeFBSEMA)_4$—S—$CH_2CH_2OOCC_{17}H_{35}$ | pasted | 6 | 4 | 4 | 0+ | 80 |
| C6 | FC-3573 | pasted | 8 | 7 | 4 | 3 | 80 |
| 13 | $(MeFBSEA)_4$—S—$CH_2CH_2OOCC_{17}H_{35}$ | new bath | 7 | 6 | 2–5* | 1 | 80 |
| 14 | $(MeFBSEMA)_4$—S—$CH_2CH_2OOCC_{17}H_{35}$ | new bath | 5 | 3 | 1–3* | 0+ | 80 |
| C7 | FC-3573 | new bath | 9 | 9 | 6 | 5 | 80 |

*Results varied depending upon the location on the treated leather sample

Examples 15–18 and Comparative Examples C8–C9

A similar series of "pasting" and "new bath" experiments were conducted as described in Examples 11–14 and Comparative Examples C6–C7 except that wool-on sheepskin garment leather was substituted for nubuck leather. In each case, the designated % of fluorochemical emulsion used was: $(MeFBSEA)_4$-S—$CH_2CH_2OOCC_{17}H_{35}$ at 6.2%, $(MeFBSEMA)_4$-S—$CH_2CH_2OOCC_{17}H_{35}$ at 6.5% and FC-3573 at 4% concentration, each concentration, each based on the weight of leather charged to the drum. Again, the emulsion concentrations were chosen so that all three fluorochemical repellents were evaluated on the same percent solids basis, based on the weight of the leather. For this leather, the following leather preparation procedures were used (again, percentages based on the weight of leather). Re-wetting: 1000% water at 40° C. for 40 minutes, then drained. Neutralization: mixture of 1000% water, 2% sodium formate and 2% sodium bicarbonate at 40° C. for 45 minutes, then drained. Dyeing/fatliquoring no fluorochemical—for "new bath": mixture of 1000% water and 2% ammonia at 50° C. for 15 minutes, followed by addition of 2% LUGANIL BROWN NGT (available from BASF Corp.) for an additional 30 minutes, followed by addition of 8% REPELAN™ WR10 (available from Cromogenia, Spain) for an additional 45 minutes, followed by addition of 1.25% formic acid for an additional 20 minutes, followed by 1% formic acid for an additional 20 minutes, then drained.

For pasting (i.e. fluorochemical emulsion with fatliquor), the following sequential procedure used was: (1) mixture of 1000% water and 2% ammonia at 50° C. for 15 minutes, (2) 2% LUGANIL™ Brown NGT added for an additional 30 minutes, (3) mixture of 1000% water, 8% REPELAN™ WR10, designated % fluorochemical emulsion and some 60° C. water added for an additional 45 minutes, (4) 1.25% formic acid for an additional 20 minutes, and (5) 1% additional formic acid for an additional 20 minutes.

For the new bath, the following procedure was used: (1) mixture of 1000% water and designated % fluorochemical emulsion at 50° C. for 45 minutes, (2) 0.5% formic acid for 15 minutes, then drained.

Results are presented in TABLE 4.

TABLE 4

| Ex. | Repellent Composition | Appl. | WR | AWR | OR | AOR | SR |
|---|---|---|---|---|---|---|---|
| 15 | $(MeFBSEA)_4$—S—$CH_2CH_2OOCC_{17}H_{35}$ | pasted | 8 | 7 | 6 | 6 | 80 |
| 16 | $(MeFBSEMA)_4$—S—$CH_2CH_2OOCC_{17}H_{35}$ | pasted | 7 | 2 | 5 | 0+ | 80 |
| C8 | FC-3573 | pasted | 9 | 8 | 6 | 3 | 80 |
| 17 | $(MeFBSEA)_4$—S—$CH_2CH_2OOCC_{17}H_{35}$ | new bath | 7 | 3 | 4 | 1 | 80 |
| 18 | $(MeFBSEMA)_4$—S—$CH_2CH_2OOCC_{17}H_{35}$ | new bath | 5 | 2 | 3 | 0+ | 80 |
| C9 | FC-3573 | new bath | 9 | 8 | 6 | 4 | 80 |

Examples 19–22 and Comparative Examples C10–C12

In Examples 19–22 and Comparative Examples C10–C11, treated nubuck leather samples from Examples 11–14 and Comparative Examples C6–C7, respectively, were evaluated for dynamic water resistance according to the Bally Penetrometer Test (to determine water penetration time in hours and percent water absorption) and for number of flexes before water penetration using the Dynamic Saline Water Resistance Test (i.e., number of Maeser flexes).

In Comparative Example C12, no treatment was applied (i.e., the fatliquor was applied without fluorochemical).

Results are presented in TABLE 5.

TABLE 5

| | | | Bally Test: | | Maeser: |
|---|---|---|---|---|---|
| Ex. | Repellent Composition | Appl. | Time | % Abs. | # Flexes |
| 19 | $(MeFBSEA)_4$—S—$CH_2CH_2OOCC_{17}H_{35}$ | pasted | >6 | 17 | >150000 |
| 20 | $(MeFBSEMA)_4$—S—$CH_2CH_2OOCC_{17}H_{35}$ | pasted | >6 | 17 | 60000 |

TABLE 5-continued

| Ex. | Repellent Composition | Appl. | Bally Test: Time | % Abs. | Maeser: # Flexes |
|---|---|---|---|---|---|
| C10 | FC-3573 | pasted | >6 | 17 | >150000 |
| 21 | (MeFBSEA)$_4$—S—CH$_2$CH$_2$OOCC$_{17}$H$_{35}$ | new bath | >6 | 18 | >150000 |
| 22 | (MeFBSEMA)$_4$—S—CH$_2$CH$_2$OOCC$_{17}$H$_{35}$ | new bath | >6 | 18 | 135000 |
| C11 | FC-3573 | new bath | >6 | 18 | >150000 |
| C12 | None | — | 180 min | 20%* | 13400 |

*after 4 hours

We claim:

1. A method of treating fibrous substrates comprising contacting the fibrous substrate with composition comprising an alkylated fluorochemical oligomeric compound comprising:
   (i) a fluorochemical oligomeric portion comprising an aliphatic backbone with a plurality of fluoroaliphatic groups attached thereto, each fluoroaliphatic group having a fully fluorinated terminal group and each independently linked to a carbon atom of the aliphatic backbone through an organic linking group;
   (ii) an aliphatic moiety having at least 12 carbon atoms; and
   (iii) a linking group which links the fluorochemical oligomeric portion to the aliphatic moiety.

2. The method of claim 1 wherein said an alkylated fluorochemical oligomeric compound comprises:
   (i) an oligomeric portion having both fluoroaliphatic and fluorine-free aliphatic pendent groups;
   (ii) an aliphatic moiety having at least 12 carbon atoms; and
   (iii) a linking group which links the oligomeric portion to the aliphatic moiety.

3. The method of claim 1 wherein said fluorochemical compounds are selected from the group consisting of:

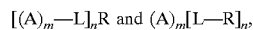

wherein m is 1 to 4 inclusive;
n is 1 to about 4 inclusive;
each L independently comprises a linking group;
R is an organic aliphatic moiety; and
A is a fluorochemical oligomeric portion of the formula:

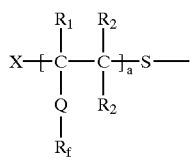

wherein
a is a number such that A is oligomeric and comprises a plurality of R$_f$ groups;
each R$_1$ is independently hydrogen, halogen, or straight chain or branched chain alkyl containing 1 to about 4 carbon atoms;
each R$_2$ is independently hydrogen or straight chain or branched chain alkyl containing 1 to about 4 carbon atoms;
each Q is a covalent bond or an organic linking group;
R$_f$ is a fluoroaliphatic group;
X is a hydrogen atom or a group derived from a free radical initiator.

4. The method of claim 2 wherein said fluorochemical compounds are selected from the group consisting of:

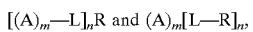

wherein m is 1 to 4 inclusive;
n is 1 to 4 inclusive;
each L independently comprises a linking group;
R is an organic aliphatic moiety; and
A is a fluorochemical oligomeric portion of the formula

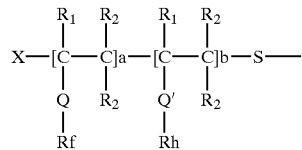

wherein the sum of a+b is a number such that A is oligomeric, each R$_1$ independently is hydrogen, halogen, or straight chain or branched chain alkyl containing 1 to about 4 carbon atoms;
each R$_2$ is independently hydrogen or straight chain or branched chain alkyl containing 1 to about 4 carbon atoms;
Q and Q' are each independently a covalent bond or an organic linking group, R$_f$ is a fluoroaliphatic group; and
R$_h$ is a fluorine-free aliphatic group.

5. The method of claim 3 wherein a is 3 to 8.

6. The method of claim 4 wherein the sum of a+b is 3 to 8.

7. The method of claim 3 wherein R$_f$ has the structure C$_o$F$_{2o+1}$, where o is 4 to 8.

8. The method of claim 3 wherein L is selected from the group of a covalent bond, straight chain, branched chain, or cyclic alkylene, arylene, aralkylene, oxy, oxo, hydroxy, thio, sulfonyl, sulfoxy, amino, imino, sulfonamido, carboxamido, carbonyloxy, urethanylene, ureylene, and combinations thereof.

9. The method of claim 3 wherein L is chosen from the group consisting of

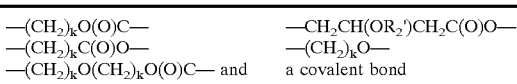

wherein each k is independently an integer from 0 to about 20, and R$_2$' is alkyl of 1 to about 20 carbon atoms.

10. The method of claim 2 comprising oligomerized units of compounds of the formula

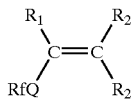

wherein $R_1$, $R_2$, $R_f$ and Q are as defined in claim 2.

11. The method of claim 3 wherein $R_f$ is a pertfluorinated alkyl group having 4 to about 8 carbon atoms.

12. The method of claim 3 wherein Q is selected from the group consisting of

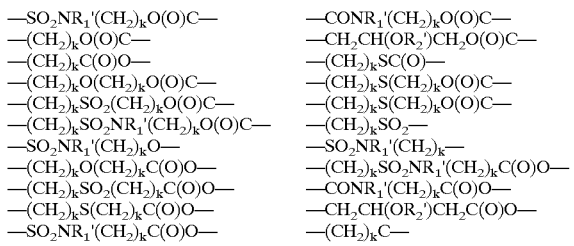

wherein each k is independently an integer from 0 to about 20, $R_1'$ is hydrogen, phenyl, or alkyl of 1 to about 4 carbon atoms, and $R_2'$ is alkyl of 1 to about 20 carbon atoms.

13. The method of claim 1 wherein R is an alkyl group having at least 12 carbon atoms.

14. The method of claim 3 wherein R is an alkyl group having from 12 to 75 carbon atoms.

15. The method of claim 1 wherein said substrate is leather.

16. The method according to claim 1 wherein said composition is in the form of an aqueous dispersion.

17. The method according to claim 16 wherein said leather is contacted with said aqueous dispersion during retanning.

18. The method of claim 1 wherein said fluorochemical oligomeric compounds have a receding contact angle to n-hexadecane of at least about 30°.

19. The method of claim 1 wherein said fluorochemical oligomeric compounds have an receding contact angle to n-hexadecane of at least about 50°.

20. The method of claim 1 wherein said composition is applied by spraying, pasting, padding, roll coating, brushing or exhausting.

21. A treated fibrous substrate comprising a coating of a composition comprising an alkylated fluorochemical oligomeric compound comprising:
(i) a fluorochemical oligomeric portion comprising an aliphatic backbone with a plurality of fluoroaliphatic groups attached thereto, each fluoroaliphatic group having a fully fluorinated terminal group and each independently linked to a carbon atom of the aliphatic backbone through an organic linking group;

(ii) an aliphatic moiety having at least 12 carbon atoms; and (iii) a linking group which links the fluorochemical oligomeric portion to the aliphatic moiety.

22. The treated substrate of of claim 21 wherein said an alkylated fluorochemical oligomeric compound comprises:
(i) an oligomeric portion having both fluoroaliphatic and fluorine-free aliphatic pendent groups;

(ii) an aliphatic moiety having at least 12 carbon atoms; and (iii) a linking group which links the oligomeric portion to the aliphatic moiety.

23. The method of claim 21 wherein said fluorochemical compounds are selected from the group consisting of:

$$[(A)_m\text{—L}]_n R \text{ and } (A)_m[\text{L—R}]_n,$$

wherein m is 1 to 4 inclusive;

n is a whole number from 1 to about 4;

each L independently comprises a linking group;

R is an organic aliphatic moiety; and

A is a fluorochemical oligomeric portion of the formula:

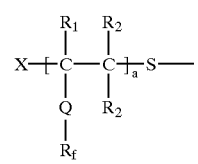

wherein a is a number such that A is oligomeric and comprises a plurality of $R_f$ groups;

each $R_1$ is independently hydrogen, halogen, or straight chain or branched chain alkyl containing 1 to about 4 carbon atoms;

each $R_2$ is independently hydrogen or straight chain or branched chain alkyl containing 1 to about 4 carbon atoms;

each Q is a covalent bond or an organic linking group;

$R_f$ is a fluoroaliphatic group;

X is a hydrogen atom or a group derived from a free radical initiator.

24. The treated substrate of claim 21 wherein a is 3 to 8.

25. The treated substrate of claim 21 wherein R is an alkyl group having at least 12 carbon atoms.

26. The treated substrate of claim 21 wherein R is an alkyl group having from 12 to 75 carbon atoms.

27. The treated substrate of claim 21 wherein said substrate is leather.

* * * * *

UNITED STATES PATENT AND TRADEMARK OFFICE
CERTIFICATE OF CORRECTION

PATENT NO. : 6,525,127 B1  
DATED : February 25, 2003  
INVENTOR(S) : Jariwala, Chetan P.

Page 1 of 1

It is certified that error appears in the above-identified patent and that said Letters Patent is hereby corrected as shown below:

Title page,  
Item [56], References Cited, OTHER PUBLICATIONS, "C.N. Davies" reference, delete "IB" and insert -- 1B --

Column 6,  
Line 52, delete the word "thereof" and insert in place thereof -- thereof. --

Column 15,  
Line 42, delete "alcohol.," and insert in place thereof -- alcohol. --

Column 18,  
Line 15, delete "88" and insert in place thereof -- 88, --  
Line 18, delete "UNSILIN$^{TM}$" and insert in place thereof -- UNLIN$^{TM}$ --  
Line 30, delete "VASO$^{TM}$" and insert in place thereof -- VAZO$^{TM}$ --

Column 22,  
Line 12, delete "(R&)" and insert in place thereof -- ($R_h$) --

Column 23,  
Line 38, delete "Compative" and insert in place thereof -- Comparative --  
Line 49, delete "$CH_2CH_2OOCC_{17}H_35$" and insert in place there of -- $CH_2CH_2OOCC_{17}H_{35}$ --

Column 29,  
Line 8, delete "pertfluorinated" and insert in place thereof -- perflurinated --

Signed and Sealed this

Twenty-fourth Day of August, 2004

JON W. DUDAS  
*Director of the United States Patent and Trademark Office*